United States Patent
McVeigh

(10) Patent No.: US 11,707,355 B2
(45) Date of Patent: Jul. 25, 2023

(54) MODULAR HEART VALVE PROSTHESIS

(71) Applicant: MEDTRONIC INC., Minneapolis, MN (US)

(72) Inventor: Cahal McVeigh, White Bear Township, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 87 days.

(21) Appl. No.: 16/885,553

(22) Filed: May 28, 2020

(65) Prior Publication Data

US 2021/0369451 A1    Dec. 2, 2021

(51) Int. Cl.
   *A61F 2/24* (2006.01)
(52) U.S. Cl.
   CPC .......... *A61F 2/2418* (2013.01); *A61F 2/2409* (2013.01); *A61F 2/2433* (2013.01)
(58) Field of Classification Search
   CPC .... A61F 2/2409; A61F 2/2418; A61F 2/2427; A61F 2/24; A61F 2002/826
   See application file for complete search history.

(56) References Cited

U.S. PATENT DOCUMENTS

| 4,340,091 | A | * | 7/1982 | Skelton | A61F 2/06 |
| | | | | | 87/8 |
| 5,332,402 | A | | 7/1994 | Teitelbaum | |
| 6,419,696 | B1 | | 7/2002 | Ortiz et al. | |
| 6,425,916 | B1 | | 7/2002 | Garrison et al. | |
| 6,530,952 | B2 | | 3/2003 | Vesely | |
| 6,730,121 | B2 | | 5/2004 | Ortiz et al. | |
| 6,767,362 | B2 | | 7/2004 | Schreck | |
| 6,790,229 | B1 | | 9/2004 | Berreklouw | |
| 6,964,684 | B2 | | 11/2005 | Ortiz et al. | |

(Continued)

FOREIGN PATENT DOCUMENTS

| WO | 2014081796 A1 | 5/2014 |
| WO | 2014080339 A1 | 6/2014 |

(Continued)

OTHER PUBLICATIONS

Extended European Search Report in corresponding EP Application No. 21176225.7, dated Oct. 1, 2021.

*Primary Examiner* — Christopher D. Prone
(74) *Attorney, Agent, or Firm* — Medler Ferro Woodhouse & Mills PLLC

(57) ABSTRACT

A modular heart valve prosthesis includes a first heart valve device and a second heart valve device. The first heart valve device includes a first valve support including a first prosthetic valve disposed within the valve support, and an anchoring frame surrounding the first valve support and coupled to the first valve support. The first prosthetic valve includes synthetic fabric leaflets having a first thickness. The second heart valve device includes a second valve support including a second prosthetic valve disposed within the second valve support. The second prosthetic valve includes tissue leaflets having a second thickness, wherein the second thickness is greater than the first thickness. In a first configuration, the second heart valve device is separate from the first heart valve device, and in a second configuration, the second heart valve device is disposed within the first valve support of the first heart valve device.

30 Claims, 15 Drawing Sheets

(56) References Cited

U.S. PATENT DOCUMENTS

| | | |
|---|---|---|
| 7,011,681 B2 | 3/2006 | Vesely |
| 7,252,682 B2 | 8/2007 | Seguin |
| 7,381,218 B2 | 6/2008 | Schreck |
| 7,524,330 B2 | 4/2009 | Berreklouw |
| 7,585,321 B2 | 9/2009 | Cribier |
| 7,611,535 B2 | 11/2009 | Woolfson et al. |
| 7,648,528 B2 | 1/2010 | Styrc |
| 7,708,775 B2 | 5/2010 | Rowe et al. |
| 7,758,640 B2 | 7/2010 | Vesely |
| 7,776,083 B2 | 8/2010 | Vesely |
| 7,846,203 B2 | 12/2010 | Cribier |
| 7,846,204 B2 | 12/2010 | Cribier |
| 8,002,825 B2 | 8/2011 | Letac et al. |
| 8,070,800 B2 | 8/2011 | Lock et al. |
| 8,052,750 B2 | 11/2011 | Tuval et al. |
| 8,057,540 B2 | 11/2011 | Letac et al. |
| 8,092,518 B2 | 1/2012 | Schreck |
| 8,142,492 B2 | 3/2012 | Forster et al. |
| 8,142,496 B2 | 3/2012 | Berreklouw |
| 8,236,049 B2 | 8/2012 | Rowe et al. |
| 8,308,798 B2 | 11/2012 | Pintor et al. |
| 8,323,335 B2 | 12/2012 | Rowe et al. |
| 8,366,766 B2 | 2/2013 | Berreklouw |
| 8,398,708 B2 | 3/2013 | Meiri et al. |
| 8,500,798 B2 | 8/2013 | Rowe et al. |
| 8,551,160 B2 | 10/2013 | Figulla et al. |
| 8,551,161 B2 | 10/2013 | Dolan |
| 8,568,473 B2 | 10/2013 | Yoganathan et al. |
| 8,591,573 B2 | 11/2013 | Barone |
| 8,591,575 B2 | 11/2013 | Cribier |
| 8,597,348 B2 | 12/2013 | Rowe et al. |
| 8,657,872 B2 | 2/2014 | Seguin |
| 8,685,086 B2 | 4/2014 | Navia et al. |
| 8,747,460 B2 | 6/2014 | Tuval et al. |
| 8,771,345 B2 | 7/2014 | Tuval et al. |
| 8,771,346 B2 | 7/2014 | Tuval et al. |
| 8,834,561 B2 | 9/2014 | Figulla et al. |
| 8,840,664 B2 | 9/2014 | Karapetian et al. |
| 8,911,493 B2 | 12/2014 | Rowe et al. |
| 8,992,604 B2 | 3/2015 | Gross et al. |
| 8,998,982 B2 | 4/2015 | Richter et al. |
| 9,017,399 B2 | 4/2015 | Gross et al. |
| 9,050,188 B2 | 6/2015 | Schweich et al. |
| 9,072,604 B1 | 7/2015 | Melnick et al. |
| 9,173,737 B2 | 11/2015 | Hill et al. |
| 9,248,016 B2 | 2/2016 | Oba et al. |
| 2001/0010017 A1 | 7/2001 | Letac et al. |
| 2002/0151970 A1 | 10/2002 | Garrison et al. |
| 2005/0137686 A1 | 6/2005 | Salahieh et al. |
| 2005/0137691 A1 | 6/2005 | Salahieh et al. |
| 2006/0195183 A1 | 8/2006 | Navia et al. |
| 2006/0293745 A1* | 12/2006 | Carpentier ............ A61F 2/2409 623/2.19 |
| 2007/0010876 A1 | 1/2007 | Salahieh et al. |
| 2008/0109073 A1 | 5/2008 | Lashinsky et al. |
| 2008/0208329 A1* | 8/2008 | Bishop ................. A61F 2/2427 623/2.11 |
| 2009/0281609 A1 | 11/2009 | Benichou et al. |
| 2010/0076548 A1* | 3/2010 | Konno ................. A61F 2/2433 623/2.1 |
| 2010/0249908 A1 | 9/2010 | Chau et al. |
| 2010/0280606 A1 | 11/2010 | Naor |
| 2010/0312333 A1 | 12/2010 | Navia et al. |
| 2011/0224785 A1 | 9/2011 | Hacohen |
| 2012/0022640 A1 | 1/2012 | Gross et al. |
| 2012/0046741 A1 | 2/2012 | Tuval et al. |
| 2012/0059458 A1 | 3/2012 | Buchbinder |
| 2012/0083839 A1 | 4/2012 | Letac et al. |
| 2012/0101571 A1 | 4/2012 | Thambar et al. |
| 2012/0150287 A1 | 6/2012 | Forster et al. |
| 2012/0203335 A1 | 8/2012 | Vesely et al. |
| 2012/0310328 A1 | 12/2012 | Olson et al. |
| 2013/0166022 A1 | 6/2013 | Conklin |
| 2013/0190865 A1 | 7/2013 | Anderson |
| 2013/0211491 A1 | 8/2013 | Berreklouw |
| 2013/0245753 A1 | 9/2013 | Alkhatib |
| 2013/0310917 A1 | 11/2013 | Richter et al. |
| 2014/0005778 A1 | 1/2014 | Buchbinder et al. |
| 2014/0172070 A1 | 6/2014 | Seguin |
| 2014/0207231 A1 | 7/2014 | Hacohen et al. |
| 2014/0214160 A1 | 7/2014 | Naor |
| 2014/0249611 A1 | 9/2014 | Carmi et al. |
| 2014/0309680 A1 | 10/2014 | Fargahi |
| 2014/0309727 A1 | 10/2014 | Lamelas et al. |
| 2014/0309730 A1 | 10/2014 | Alon et al. |
| 2014/0324164 A1 | 10/2014 | Gross et al. |
| 2014/0358222 A1 | 12/2014 | Gorman et al. |
| 2014/0379074 A1 | 12/2014 | Spence et al. |
| 2015/0112433 A1 | 4/2015 | Schweich et al. |
| 2015/0148896 A1 | 5/2015 | Karaptian et al. |
| 2015/0173898 A1 | 6/2015 | Drasler et al. |
| 2017/0016288 A1 | 1/2017 | Culver et al. |

FOREIGN PATENT DOCUMENTS

| | | |
|---|---|---|
| WO | 2015164061 A1 | 10/2015 |
| WO | 2020073056 A1 | 4/2020 |

* cited by examiner

MODULAR HEART VALVE PROSTHESIS

FIELD OF THE INVENTION

The present invention relates to prostheses and methods for manufacturing prostheses. More particularly, the present invention relates to a structural component such as a stent, stent ring or frame of a prosthesis such as a stent-graft prosthesis or a heart valve prosthesis.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses can be delivered while in a radially compressed configuration so that the valve prosthesis can be advanced through the patient's vasculature. Once positioned at the treatment site, the valve prosthesis can be expanded to engage tissue at the diseased heart valve region to, for instance, hold the valve prosthesis in position. While these valve prostheses offer minimally invasive methods for heart valve repair and/or replacement, challenges remain to providing effective, less invasive, smaller crossing profile prosthetic delivery systems. Recent heart valve prosthesis designs have incorporated additional graft material to aid in sealing to prevent paravalvular leakage (PVL). However, this additional material adds to the crossing profile of the heart valve prosthesis. The increased crossing profile, especially for radial interventions and inter-atrial septum puncture, limits the size of the heart valve prosthesis and/or the feasibility of transcatheter delivery.

In an example, as a heart valve prosthesis is compressed/loaded for delivery, portions of the frame of the heart valve prosthesis are pushed closer and closer together to obtain the desired crossing profile. On occasion, during loading, the heart valve prosthesis is compressed to the point where the frame can no longer find space along the desired circumference of the heart valve prosthesis and portions of the frame of the heart valve prosthesis will buckle, fold, or otherwise deform radially inward. When the heart valve prosthesis deforms radially inward as described above, the frame is exposed to increased stresses that may damage the frame and negatively affect the structural integrity of the heart valve prosthesis.

Accordingly, there is a need for heart valve prostheses that more efficiently compress to smaller profiles without damaging the frame of the heart valve prosthesis.

BRIEF SUMMARY OF THE INVENTION

Embodiments hereof are directed to a modular heart valve prosthesis including a first heart valve device and a second heart valve device. The first heart valve device includes a first valve support including a first prosthetic valve disposed within the valve support, and an anchoring frame surrounding the first valve support and coupled to the first valve support. The first prosthetic valve includes synthetic fabric leaflets having a first thickness. The second heart valve device includes a second valve support including a second prosthetic valve disposed within the second valve support. The second prosthetic valve includes tissue leaflets having a second thickness, wherein the second thickness is greater than the first thickness. In a first configuration, the second heart valve device is separate from the first heart valve device, and in a second configuration, the second heart valve device is disposed within the first valve support of the first heart valve device.

In embodiments of the modular valve prosthesis according to any of the embodiments, the first heart valve device may be self-expanding and the second heart valve device may be balloon expandable.

In embodiments of the modular valve prosthesis according to any of the embodiments, the first heart valve device may be self-expanding and the second heart valve device may self-expanding.

In embodiments of the modular valve prosthesis according to any of the embodiments herein, the synthetic fabric leaflets of the first prosthetic valve are formed from material selected from the group consisting of polyester, polyethylene terephthalate (PET, e.g. DACRON), polytetrafluoroethylene (PTFE), polyurethane, cloth materials, nylon blends, and polymeric materials.

In embodiments of the modular valve prosthesis according to any of the embodiments herein the tissue leaflets of the second prosthetic valve are formed from material selected from the group consisting of bovine pericardium tissue and porcine pericardium tissue.

In embodiments of the modular valve prosthesis according to any of the embodiments herein, the first thickness is in the range of about 0.04 mm to about 0.1 mm. In embodiments of the modular valve prosthesis according to any of the embodiments herein, the first thickness is about 0.07 mm.

In embodiments of the modular valve prosthesis according to any of the embodiments herein, the second thickness is in the range of about 0.35 mm to about 0.5 mm.

In embodiments of the modular valve prosthesis according to any of the embodiments herein, the first heart valve device has a crimped diameter of approximately 27 Fr.

In embodiments of the modular valve prosthesis according to any of the embodiments herein, the second heart valve device has a crimped diameter of approximately 14 Fr.

In embodiments of the modular valve prosthesis according to any of the embodiments herein, the second heart valve device further includes a skirt disposed on an outer surface of the second valve support, wherein in the second configuration, the skirt seals against an inner surface of the first valve support.

In embodiments of the modular valve prosthesis according to any of the embodiments herein, the first valve support and the second valve support are both generally cylindrical.

In embodiments of the modular valve prosthesis according to any of the embodiments herein, the first valve support has an hourglass shape with a first diameter at an inflow portion thereof, a second diameter at a central portion thereof, and a third diameter at an outflow portion thereof, wherein the first and third diameters are each larger than the second diameter, and wherein the second valve support has a corresponding hourglass shape.

In embodiments of the modular valve prosthesis according to any of the embodiments herein, the first valve support has a reverse hourglass shape with a first diameter at an inflow portion thereof, a second diameter at a central portion thereof, and a third diameter at an outflow portion thereof, wherein the first and third diameters are each smaller than the second diameter, and wherein the second valve support has a corresponding reverse hourglass shape.

In embodiments of the modular valve prosthesis according to any of the embodiments herein, the second valve support includes a brim at an inflow end thereof, wherein the brim is parallel to a central longitudinal axis of the second valve support with the second heart valve device in a radially compressed configuration, wherein the brim is disposed radially outward at a non-zero angle with respect to the central longitudinal axis with the second heart valve device in a radially expanded configuration, and wherein in the second configuration of the second heart valve device, the brim is proximal of an inflow end of the first valve support. In embodiments, the non-zero angle of the brim with the second heart valve device in the radially expanded configuration is between 30 and 90 degrees.

In embodiments of the modular valve prosthesis according to any of the embodiments herein, the second heart valve device further includes barbs extending radially outward from an outer surface of the second valve support such that with the second heart valve device in the second configuration, the barbs engage the first valve support.

Embodiments hereof are also directed to a method of delivering and deploying a modular heart valve prosthesis. The method includes delivering a first heart valve device in a radially compressed configuration to a site of a native heart valve. The first heart valve device includes a first valve support including a first prosthetic valve comprising synthetic fabric leaflets disposed within the valve support and an anchoring frame surrounding the first valve support and coupled to the first valve support. The method further includes deploying the first heart valve device by radially expanding the first heart valve device such that the anchoring frame is disposed within native leaflets of the native heart valve. After deploying the first heart valve device, the method further includes delivering a second heart valve device in a radially compressed configuration to within the first valve support, the second heart valve device including a second valve support and a second prosthetic valve comprising tissue leaflets disposed within the second valve support. The method further includes deploying the second heart valve device by radially expanding the second valve support such that the second valve support engages the first prosthetic valve and the first valve support.

In embodiments of methods of delivering and deploying a modular heart valve prosthesis according to any of the embodiments hereof, the step of deploying the first heart valve device comprises releasing the first heart valve device from a sheath such that the first heart valve device self-expands.

In embodiments of methods of delivering and deploying a modular heart valve prosthesis according to any of the embodiments hereof, the step of deploying the second heart valve device comprises radially expanding the second valve support with a balloon.

In embodiments of methods of delivering and deploying a modular heart valve prosthesis according to any of the embodiments hereof, the first heart valve device is disposed in a first catheter for the step of delivering the first heart valve device.

In embodiments of methods of delivering and deploying a modular heart valve prosthesis according to any of the embodiments hereof, after the step of deploying the first heart valve device from a first catheter, the first catheter is withdrawn from the site of the native heart valve.

In embodiments of methods of delivering and deploying a modular heart valve prosthesis according to any of the embodiments hereof, after the steps of deploying the first heart valve device from a first catheter and withdrawing the first catheter, the second heart valve delivered in a second catheter.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of embodiments hereof is in the context of the treatment of heart valves such as the pulmonary, aortic, mitral, or tricuspid valve, the invention may also be used in any other body passageways where it is deemed useful. Furthermore, there is no intention to be bound by any expressed or implied theory presented in the preceding technical field, background, brief summary or the following detailed description.

Figure 1:
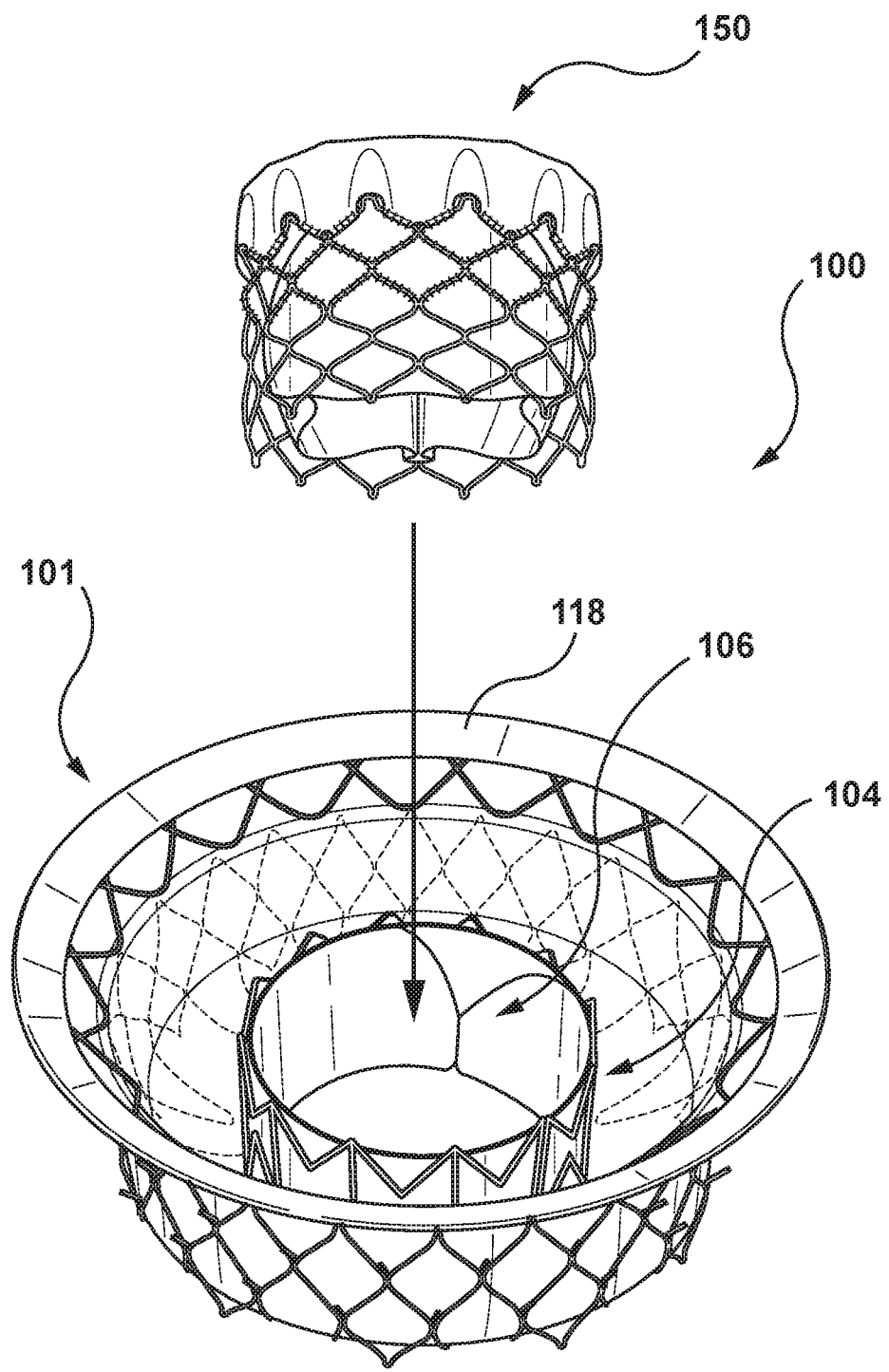
FIG. 1 depicts perspective view of a modular heart valve prosthesis in accordance with an embodiment hereof.

FIG. 1 is a perspective view of an exemplary heart valve prosthesis 100 for use in embodiments hereof. The heart prosthesis 100 is a modular heart valve prosthesis including a first heart valve device 101 and a second heart valve device 150. As can be seen in FIG. 1, the second heart valve device 150 is separate from the first heart valve device 101 until the second heart valve device 150 is disposed within the first heart valve device in vivo, as will be explained in more detail below.

The first heart valve device 101 as illustrated and described herein is not limited to the specific embodiments described herein. It is understood that any number of alternate heart valve prostheses and/or stent assemblies can be used with the invention described herein. The first heart valve device is merely exemplary and is similar to heart valve prostheses described in more detail in U.S. Pat. No. 9,034,032, WIPO Publication No. WO 2014/144937, and WIPO Publication No. WO 2013/059747, each of which is herein incorporated by reference in its entirety. Other non-limiting examples of transcatheter heart valve prostheses that may be used as the first heart valve device described herein are described in U.S. Patent Application Publication No. 2012/0101572, U.S. Patent Application Publication No. 2012/0035722, U.S. Patent Application Publication No. 2006/0265056, U.S. Patent Application Publication No. 2007/0239266, and U.S. Patent Application Publication No. 2007/0239269, each of which is incorporated by reference herein in its entirety.

Figure 2:
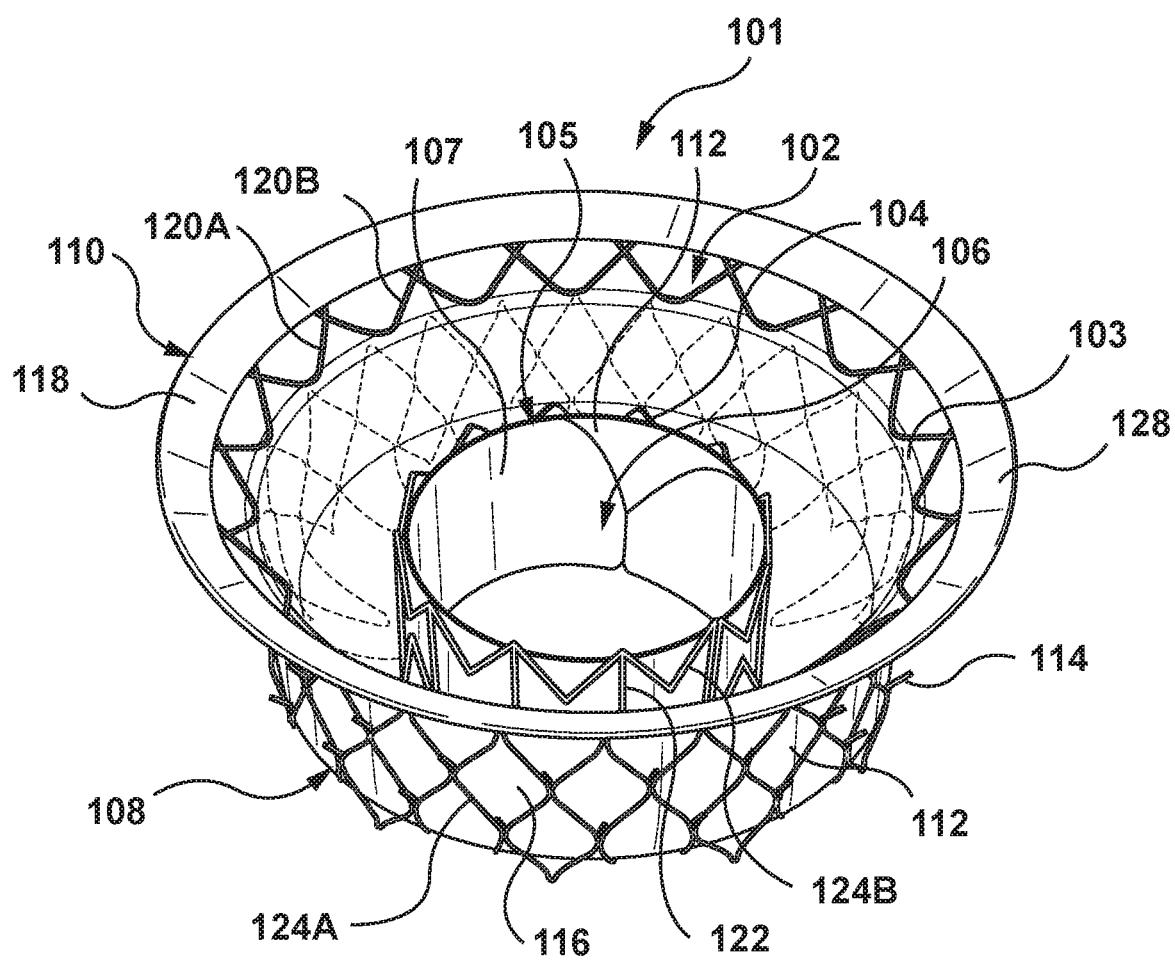
FIG. 2 depicts a perspective view of a first heart valve device of the modular heart valve prosthesis of FIG. 1 according to an embodiment hereof.
Figure 4:
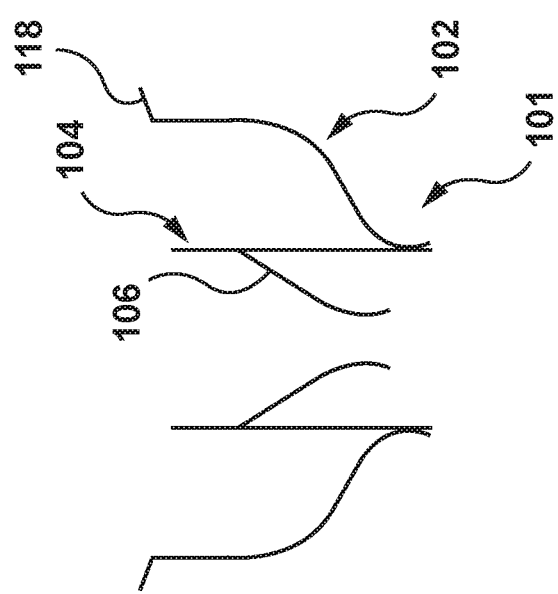
FIG. 4 depicts a schematic side view of the first heart valve device of FIG. 2 of the modular heart valve prosthesis of FIG. 1.

As shown in FIGS. 1, 2 and 4, the first heart valve device 101 includes an anchoring member or frame 102 at least partially surrounding and coupled to a valve frame or support 104. The first heart valve device 101 further includes a first or temporary prosthetic valve 106 coupled to, mounted within, or otherwise carried by the valve support 104. The first heart valve device 101 is configured for placement within a native mitral valve and includes a downstream or distal end portion, referred to herein as an outflow portion 108, and an upstream or proximal end portion, referred to herein as an inflow portion 110. The first heart valve device 101 may also include tissue engaging elements 114. For example, the tissue engaging elements 114 may be spikes or barbs disposed on an outer wall or surface of the anchoring frame 102 and extending in an upward and/or radially outward direction to engage, and in some embodiments, penetrate the native tissue to facilitate retention or maintain position of the device in a desired implanted location.

The anchoring frame 102 is a generally tubular component or stent. In the embodiment shown in FIGS. 1-2, the anchoring frame 102 has a funnel-like or hyperboloid shape or profile. Further, the anchoring frame 102 includes openings 116 that may be diamond-shaped. The anchoring frame 102 may be formed by a laser-cut manufacturing method and/or another conventional frame forming methods. For example, the anchoring frame 102 may be laser cut from a single metal tube into the desired geometry, creating a tubular scaffold of interconnected struts 124A that form the openings 116. The anchoring frame 102 may then be shaped into a desired configuration, e.g. funnel-like or hyperboloid shape, using known shape-setting techniques for such materials. It will be understood the anchoring frame 102 may have other shapes and configurations. For example, in another embodiment, the anchoring frame 102 may include a plurality of posts connected circumferentially by a plurality of struts as described herein with respect to the valve support 104.

The first heart valve device 101 may further include a brim 118. The brim 118 is disposed at the inflow portion 110 of the first heart valve device 101 and is attached to and extends from an inflow end 103 of the anchoring frame 102. The brim 118 is a flared lip or ridge of the anchoring frame 102 that extends at least partially radially outward relative to the anchoring frame 102. The brim 118 may be disposed at an angle relative to the outer wall or surface of the anchoring frame 102, for example, between 30 and 90 degrees, or between 40 and 50 degrees. In the embodiment shown in FIGS. 1-2, the brim 118 includes two sinusoidal rings 120A, 120B and a sealing component 128 disposed over or covering at least a downstream surface of the sinusoidal rings 120A, 120B. The sinusoidal rings 120A, 120B are disposed out of phase relative to each other, and may be woven together or may be disposed in an overlapping manner and coupled together. The sealing component 128 may be formed from a suitable natural or biological material such as pericardium or another membranous tissue including, but not limited to intestinal submucosa. Alternatively, the sealing component 128 may be a low-porosity woven fabric, such as polyester, polyethylene terephthalate (PET), or polytetrafluoroethylene (PTFE), or may be a knit or woven polyester, such as a polyester or PTFE knit.

The valve support 104 may be a generally tubular component or stent that supports the temporary prosthetic valve 106 within the interior of the valve support 104. In some embodiments, the valve support 104 includes a plurality of posts 122 connected circumferentially by a plurality of struts 124B. The plurality of posts 122 and the plurality of struts 124B may be arranged in a variety of geometrical patterns that expand and provide sufficient resilience and column strength for maintaining the integrity of the temporary prosthetic valve 106. Generally, the plurality of posts 122 extend along an axial direction generally parallel to the central longitudinal axis of the first heart valve device 100. Further, the plurality of posts 122 extend axially or longitudinally across multiple rows of the plurality of struts 124B to provide column strength to the valve support 104. The plurality of struts 124B extend circumferentially around and transverse to the longitudinal axis LA1. As will be understood, the valve support 104 may have other shapes and configurations. For example, in another embodiment, the valve support 104 may be laser cut from a single metal tube into the desired geometry, creating a tubular scaffold of interconnected struts.

In embodiments hereof, both the anchoring frame 102 and the valve support 104 are self-expanding to return to a radially expanded state from a radially compressed state and may be made from materials such as, but not limited to stainless steel, a pseudo-elastic metal such as a nickel titanium alloy (e.g. NITINOL), or a so-called super alloy, which may have a base metal of nickel, cobalt, chromium, or other metal. "Self-expanding" as used herein means that a structure/component has a mechanical memory to return to the radially expanded configuration or state as described herein. Thus, the first heart valve device 101 has a radially compressed configuration for delivery within a delivery system and the radially expanded configuration for deployment within an annulus of the native heart valve site.

As previously described, the first heart valve device 100 includes the temporary prosthetic valve 106 within the interior of the valve support 104. In an embodiment hereof, the temporary prosthetic valve 106 is positioned adjacent to an inflow end 105 of the valve support 104. The temporary prosthetic valve 106 is configured as a one-way valve to allow blood flow in one direction and thereby regulate blood flow therethrough. The temporary prosthetic valve 106 is capable of blocking flow in one direction to regulate flow therethrough via valve leaflets 107 that may form a bicuspid or tricuspid replacement valve. The temporary prosthetic valve 106 is referred to as a temporary valve because the valve leaflets are made of relatively thin material such that the first heart valve device 101 may be radially compressed to a smaller diameter or profile radially compressed configuration for delivery. Such a smaller diameter or profile is particularly useful for mitral valve prostheses because a transseptal approach to the native mitral valve requires a tight turning radius. A larger mitral valve prosthesis may have difficulty making the required turn in the radially compressed configuration. Thus, the valve leaflets 107 of the temporary prosthetic valve 106 may be made of thin synthetic materials such as, but not limited to, polyester, polyethylene terephthalate (PET), polytetrafluoroethylene (PTFE), polyurethane, cloth materials, nylon blends, and polymeric materials. In a particular example, the valve leaflets 107 are formed of polyethylene terephthalate (PET) fabric. The valve leaflets 107 have a thickness in the range of about 0.04 mm to about 0.10 mm. In an embodiment, the valve leaflets 107 have a thickness of approximately 0.07 mm. The valve leaflets 107 are sutured or otherwise securely and sealingly attached to an inner circumference of the valve support 104 and/or a graft material 112 which encloses or lines the valve support 104. The terms "approximately" and "about" as used herein are used to encompass ranges and sizes within 10% of the sizes listed.

The first heart valve device 101 may also include one or more layers of the graft material 112. The graft material 112 may be coupled to the anchoring frame 102 and/or to the valve support 104 to prevent paravalvular leaks between the first heart valve device 101 and the native tissue and/or between the anchoring frame 102 and the valve support 104. The graft material 112 is formed from a suitable natural or biological graft material such as pericardium or another membranous tissue including, but not limited to intestinal submucosa. Alternatively, the graft material 112 may be a low-porosity woven fabric, such as polyester, polyethylene terephthalate (PET), or polytetrafluoroethylene (PTFE), which creates a one-way fluid passage when attached to the frame. In one embodiment, the graft material 112 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. In the embodiment of FIGS. 1-2, the first heart valve device 101 includes two layers of the graft material 112. More precisely, a first layer 112A is coupled to the anchoring frame 102 and extends around an inner wall or surface of the anchoring frame 102 while a second layer 112B is coupled to the valve support 104 and extends around an inner wall or surface of the valve support 104. However, this is by way of example and not limitation. In other embodiments, the first heart valve device 101 can have a greater or lesser number of layers of graft material. For example, the graft material 112 may be coupled to an inner and/or an outer surface of either the anchoring frame 102 and/or the valve support 104 in any combination.

As noted above, it is desirable for the first heart valve device 101 to have a small diameter or profile when in the radially compressed configuration. Therefore, as described above, the first heart valve device 101 includes a thin prosthetic valve 106 disposed within the valve support 104, approximately 0.07 mm in thickness. A first heart valve device 101 of the design described above with the prosthetic valve 106 having a 0.07 mm thickness can be radially compressed to approximately 27 Fr outer diameter. However, such a thin prosthetic valve 106 cannot serve as a long-term replacement valve for the native mitral valve due to limited durability of such a thin fabric prosthetic valve. However, the prosthetic valve 106 can serve as a temporary or short term valve.

Figure 3:
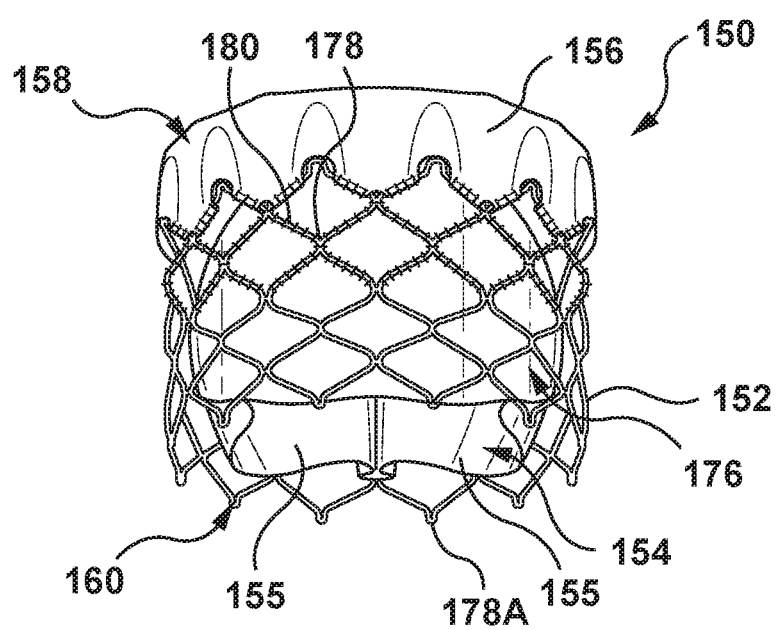
FIG. 3 depicts a perspective view of a second heart valve device of the modular heart valve prosthesis of FIG. 1 according to an embodiment hereof.

Thus, as described in more detail below, the first heart valve device 101 with the temporary prosthetic valve 106 is delivered and deployed at the native mitral valve. The second heart valve device 150, as shown in FIGS. 1 and 3, is thereafter delivered and deployed within the valve support 104 of the first heart valve device 101 to form the heart valve prosthesis 100. The second heart valve device 150 is thus separate from the first heart valve device 101 until the second heart valve device 150 is delivered to and deployed within the already deployed first heart valve device 101.

The second heart valve device 150 may be generally tubular. The second heart valve device 150 includes a valve support or frame 152 and a second or permanent prosthetic valve 154 disposed within and coupled to the frame 152. The second heart valve device 150 includes an inflow end 158 and an outflow end 160. The second heart valve device 150 may further include a skirt 156 coupled to the valve support 152.

The valve support 152 may be a generally tubular component or stent that supports the prosthetic valve 154 within the interior of the valve support 152. The valve support 152 is preferably balloon or mechanically expandable for improved interaction with the valve support 104 of the first heart valve device 101. In other words, the valve support 152 is made from a material that is plastically deformable such that the valve support requires mechanical or balloon expansion and that upon such expansion, the valve support 152 maintains the expanded configuration. However, this is not meant to be limiting, and the valve support 152 may instead be self-expanding. As described in further detail below, the cylindrical shape of both the valve support 104 of the first heart valve device 101 and the valve support 152 of the second heart valve device 150 may not provide sufficient support for the second heart valve device 150 if the second heart valve device is self-expanding. However, features described below may be included in the second heart valve device 150 to ensure proper engagement between the valve support 104 of the first heart valve device 101 and the valve support 152 of the second heart valve device 150. For example, and not by way of limitation, over-sizing of the valve support 152, barbs added to the second heart valve device 150, and/or a brim added to the second heart valve device 150, all described in further detail below, may be utilized. The valve support 152 may be formed of stainless steel or other suitable metals, such as platinum iridium, cobalt chromium alloys such as MP35N, or various types of polymers or other materials known to those skilled in the art, including said materials coated with various surface deposits to improve clinical functionality.

In some embodiments, the valve support 152, when expanded, a diameter of the inflow end 158 of the valve support 152 can be the same as a diameter of the outflow end 160 of the valve support 152. The valve support 152 can be formed by a laser-cut manufacturing method and/or another conventional stent forming method as would be understood by one of ordinary skill in the art. The cross-section of the valve support 152 can be circular, ellipsoidal, rectangular, hexagonal, square, or other polygonal shape. It is preferable that the cross-sectional shape of the valve support 152 matches the cross-sectional shape of the valve support 104, and that such a shape be circular.

In an embodiment, the valve support 152 may be formed with a plurality of struts 180 and a plurality of bends or crowns 178 being formed between adjacent pairs struts 180. The struts 180 and the crowns 178 may be formed into multiple rows of struts and crowns. In embodiments, a node is formed between crowns of adjacent rows. In the embodiment shown, there are seven rows of struts 180 and crowns 178, but this is not meant to be limiting, and there can more or fewer rows. The struts 180 and crowns 178 of adjacent rows side openings 182. In the embodiment shown, the inflow end 158 of the valve support 152 includes twelve crowns 178, but this is not meant to be limiting, and the valve support 152 can include more of fewer crowns 178A at the inflow end 158. In an embodiment, the outflow end 160 of the valve support 152 may also include twelve endmost outflow crowns 178A. In other embodiments, the outflow portion 164 may include fewer or more endmost outflow crowns 178, for example, six endmost outflow crowns 178A.

The description above of the valve support 152 is merely exemplary and not meant to be limiting. In particular, the specific structure of struts, crowns, and axial frame members is not meant to be limiting. In other examples, the valve support 152 of the second valve device 150 may be similar in structure to the valve support 104 of the first heart valve device 101, except that it is mechanically or balloon expandable, as described above.

The second or permanent prosthetic valve 154 is disposed within and secured to the valve support 152. The prosthetic valve 154 is configured as a one-way valve to allow blood flow in one direction and thereby regulate blood flow therethrough. The prosthetic valve 154 is capable of blocking flow in one direction to regulate flow therethrough via valve leaflets 155 that may form a bicuspid or tricuspid replacement valve.

As noted above, the second or permanent prosthetic valve 154 is intended to function within the native valve as a replacement valve for an extended period of time. By "permanent", as used herein, it is not intended that the second prosthetic valve 154 last forever. Instead, it is meant to last the typical life of a prosthetic replacement valve for use in human hearts. Thus, the valve leaflets 155 of the prosthetic valve 154 are made of more durable, and thicker material than the valve leaflets 107 of the temporary prosthetic 106 described above. For example, the valve leaflets 107 of the prosthetic valve 154 may be of biologic tissue such as pericardial tissue or xenograft valve tissue such as bovine pericardium or porcine pericardium. The valve leaflets 155 of the prosthetic valve 154 have a thickness in the range of about 0.35 mm to about 0.50 mm. In a particular, example, the valve leaflets 155 are bovine pericardium tissue approximately 0.4 mm in thickness.

As noted above, the second heart valve device 150 may also include a skirt 156 coupled to the valve support 152. The skirt 156 may be one or more layers of a graft material. The graft material of the skirt 156 may be coupled to the valve support 152 to provide a more secure engagement between the second heart valve device 150 and the valve support 104 of the first heart valve device 101, and to prevent paravalvular leaks between the second heart valve device 150 and valve support 104 of the first heart valve device 101. The skirt 156 may be formed from a suitable natural or biological graft material such as pericardium or another membranous tissue including, but not limited to intestinal submucosa. Alternatively, the skirt 156 may be a low-porosity woven fabric, such as polyester, polyethylene terephthalate (PET), or polytetrafluoroethylene (PTFE), which creates a one-way fluid passage when attached to the frame. In the embodiment of FIGS. 1 and 3, the skirt 156 of the second heart valve device 150 includes two layers of graft material. More precisely, a first layer is coupled to the inner surface of the valve support 152 and a second layer is coupled to the outer surface of the valve support 152. However, this is by way of example and not limitation. In other embodiments, the skirt 156 may have a single layer, more than two layers, or may be excluded.

Figure 9:
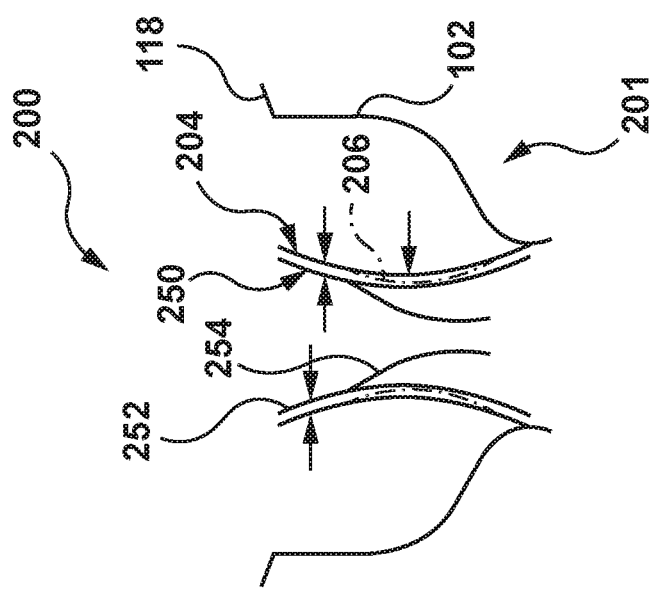
FIG. 9 depicts a schematic side view of the second heart valve device of FIG. 8 deployed within the first heart valve device of FIG. 7 to form a modular heart valve prosthesis according to an embodiment hereof.
Figure 8:
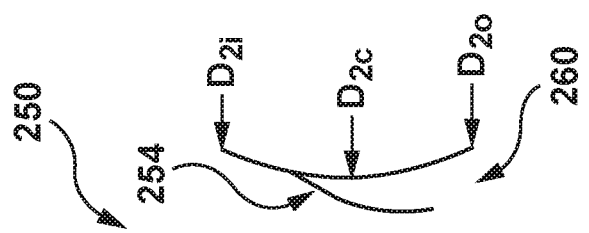
FIG. 8 depicts a schematic side view of a second heart valve device configured to be deployed within the first heart valve device of FIG. 7 to form a modular heart valve prosthesis.
Figure 7:
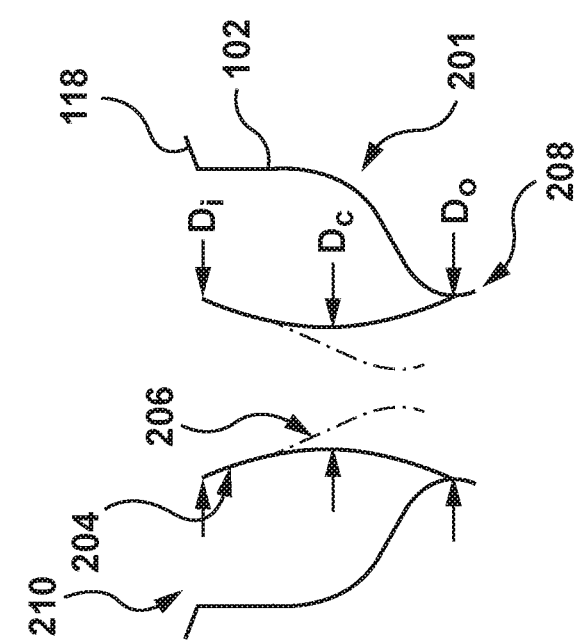
FIG. 7 depicts a schematic side view of a first heart valve device of a modular heart valve prosthesis according to an embodiment hereof.

FIGS. 7-9 schematically depict a modular heart valve prosthesis 200 according to another embodiment hereof. Similar to the modular heart valve prosthesis 100, the modular heart valve prosthesis 200 includes a first heart valve device 201 and a second heart valve device 250 configured to be deployed within the first heart valve device 201, as shown in FIG. 9.

As shown in FIGS. 7 and 9, the first heart valve device 201 of the modular heart valve prosthesis 200 includes an anchoring member or frame 102 at least partially surrounding and coupled to a valve frame or support 204. The first heart valve device 201 further includes a first or temporary prosthetic valve 206 coupled to, mounted within, or otherwise carried by the valve support 204. The first heart valve device 201 is configured for placement within a native mitral valve and includes a downstream or distal end portion, referred to herein as an outflow portion 208, and an upstream or proximal end portion, referred to herein as an inflow portion 210.

The anchoring member 102 of the first heart valve device 201 is numbered the same as the anchoring member 102 of the first heart valve device of 101 of the modular heart valve prosthesis 100 because it is substantially the same as the anchoring member 102 of the first heart valve device 101. Therefore, the detailed description thereof will not be repeated for the modular heart valve prosthesis 200, and all details, descriptions, variations, and additional items described with respect to the anchoring member 102 of the modular heart valve prosthesis 100 (such as, but not limited to the brim 118, tissue engaging elements 114, graft material 112, sealing component 128, etc.) may be included and incorporated in the anchoring member 102 of the modular heart valve prosthesis 200.

The valve support 204 of the first heart valve device 201 of the modular heart valve prosthesis 200 may be a generally tubular component or stent that supports a temporary prosthetic valve 206 within the interior of the valve support 204. In some embodiments, the valve support 204 may be any structure of a stent, including longitudinal posts, circumferential struts and crowns, and other structural features known to those skilled in the art. The valve support 204 may be similar in structure to the valve support 104, except for the shape thereof. In particular, as can be seen in FIG. 4, the valve support 104 is generally cylindrical, whereas, as can be seen in FIG. 7, the valve support 204 is generally hourglass in shape. In particular, the valve support 204 includes a first diameter $D_i$ at an inflow end thereof, a second diameter $D_c$ in a central portion thereof, and a third diameter $D_o$ at an outflow end thereof, wherein the first and third diameters $D_i$ and $D_o$ are larger than the second diameter $D_c$. In embodiments hereof, both the anchoring frame 102 and the valve support 204 of the first heart valve device 201 are self-expanding to return to a radially expanded state from a radially compressed state and may be made from materials such as, but not limited to stainless steel, a pseudo-elastic metal such as a nickel titanium alloy (e.g. NITINOL), or a so-called super alloy, which may have a base metal of nickel, cobalt, chromium, or other metal. "Self-expanding" as used herein means that a structure/component has a mechanical memory to return to the radially expanded configuration or state as described herein. Thus, the first heart valve device 201 has a radially compressed configuration for delivery within a delivery system and the radially expanded configuration for deployment within an annulus of the native heart valve site.

As previously described, the first heart valve device 201 includes the temporary prosthetic valve 206 within the interior of the valve support 204. The temporary prosthetic valve 206 is configured as a one-way valve to allow blood flow in one direction and thereby regulate blood flow therethrough. The temporary prosthetic valve 206 is capable of blocking flow in one direction to regulate flow therethrough via valve leaflets 207 that may form a bicuspid or tricuspid replacement valve. The temporary prosthetic valve 206 is referred to as a temporary valve because the valve leaflets are made of relatively thin material such that the first heart valve device 201 may be radially compressed to a smaller diameter or profile radially compressed configuration for delivery. Such a smaller diameter or profile is particularly useful for mitral valve prostheses because a transseptal approach to the native mitral valve requires a tight turning radius. A larger mitral valve prosthesis may have difficulty making the required turn in the radially compressed configuration. Thus, the valve leaflets 207 of the temporary prosthetic valve 106 may be made of thin synthetic materials such as, but not limited to, polyester, polyethylene terephthalate (PET), polytetrafluoroethylene (PTFE), polyurethane, cloth materials, nylon blends, and polymeric materials. In a particular example, the valve leaflets 107 are formed of polyethylene terephthalate (PET) fabric. The valve leaflets 107 have a thickness in the range of about 0.04 mm to about 0.10 mm. In an embodiment, the valve leaflets 107 have a thickness of approximately 0.07 mm. The valve leaflets 207 are sutured or otherwise securely and sealingly attached to an inner circumference of the valve support 204 and/or a graft material (not shown) which encloses or lines the valve support 204.

As noted above, it is desirable for the first heart valve device 201 to have a small diameter or profile when in the radially compressed configuration. Therefore, as described above, the first heart valve device 201 includes a thin prosthetic valve 206 disposed within the valve support 204, approximately 0.07 mm in thickness. However, such a thin prosthetic valve 206 cannot serve as a long-term replacement valve for the native mitral valve due to limited durability of such a thin fabric prosthetic valve. However, the prosthetic valve 206 can serve as a temporary or short term valve.

Thus, as described in more detail below, the first heart valve device 201 with the temporary prosthetic valve 206 is delivered and deployed at the native mitral valve. The second heart valve device 250, as shown in FIGS. 8 and 9, is thereafter delivered and deployed within the valve support 204 of the first heart valve device 201 to form the modular heart valve prosthesis 200. The second heart valve device 250 is thus separate from the first heart valve device 201 until the second heart valve device 250 is delivered to and deployed within the already deployed first heart valve device 201.

The second heart valve device 250 may be generally tubular. The second heart valve device 250 includes a valve support or frame 252 and a second or permanent prosthetic valve 254 disposed within and coupled to the frame 252. The second heart valve device 250 includes an inflow end 258 and an outflow end 260. The second heart valve device 250 may further include a skirt (not shown) coupled to the valve support 252.

Figure 5:
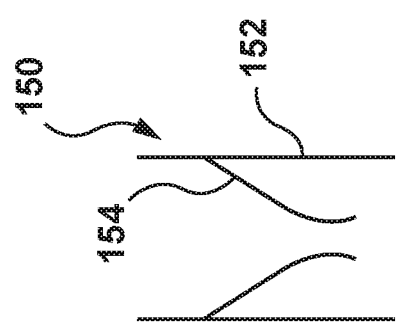
FIG. 5 depicts a schematic side view of the second heart valve device of FIG. 3 of the modular heart valve prosthesis of FIG. 1.

The valve support 252 may be a stent or frame that supports the prosthetic valve 254 within the interior of the valve support 252. The valve support 252 may be any stent structure including components such as, but not limited to, struts, bends/crowns, longitudinal bars, and other structural features known to those skilled in the art. The valve support 252 of the second valve device 250 may be similar to the valve support 152 of the embodiment of FIGS. 1-6 except that the valve support 152 is generally cylindrical, as shown in FIG. 5, and the valve support 252 has a hourglass shape, as shown in FIGS. 8 and 9. Thus, the valve support 252 includes a first diameter $D_{2i}$ at the inflow end thereof, and second diameter $D_{2c}$ at a central portion thereof, and the third diameter $D_{2o}$ at the outflow end thereof, the first and third diameters $D_{2i}$, $D_{2o}$ being larger than the second diameter $D_{2c}$.

Thus, the valve support 252 of the second valve device 250 has a similar hourglass shape as the valve support 204 of the first heart valve device 201. The hourglass shape of each valve support 204/252 enables a more secure connection between the valve support 252 and the valve support 204 when the valve support 252 is deployed within the valve support 204, as shown in FIG. 9. The corresponding hourglass shapes enable the use of a self-expanding valve support 252 with less of a likelihood of the valve support 252 of the second heart valve device 250 moving or migrating after deployment within the valve support 204 than if the valve supports were cylindrical.

To further enhance the engagement between the valve support 252 and the valve support 204 when both are self-expanding, the valve support 252 of the second heart valve device 250 may be oversized with respect to the valve support 204 of the first heart valve device 201. In other words, with self-expanding supports or frames, the support is configured to expand to a pre-set diameter when released from an outside constraint, such as a sheath. In the present situation, the valve support 204 of the first heart valve device 201 expands to its pre-set diameter, for example and not by way of limitation, 23 mm for the second diameter $D_c$. The valve support 252 of the second heart valve device 250 may be oversized in its pre-set expanded diameter such that its pre-set expanded diameter without any outside constraints is, for example and not by way of limitation, 27 mm for its second diameter $D_{2c}$. Thus, as described in more detail below, with the first heart valve device 201 deployed such that the valve support 204 radially expanded to its unconstrained diameter, the second heart valve device 250 is deployed within the valve support 204, such as by releasing the second heart valve device 250 to allow the valve support 252 of the second heart valve device 250 self-expand. Thus, the valve support 252 attempts to expand to its unconstrained diameter of, for example, 27 mm. However, when the valve support 252 reaches the diameter of 23 mm, the valve support 252 contacts the valve support 204. Being self-expanding, the valve support 252 continues to attempt to radially expand against a radially inward force of the valve support 204 which is pre-set to a smaller diameter, for example, 23 mm, as explained above. The radially outward force of the valve support 252 attempting to self-expand against the opposing radially inward force of the valve support 204 remaining at its pre-set diameter creates opposing forces, as depicted by the arrows in FIG. 9, that tend to keep the valve support 252 engaged with the valve support 204, thereby minimizing the risk of migration of the valve support 252. Although the oversizing discussed above, specifically mentions the second diameters $D_c$ and $D_{2c}$ of the valve support 204 and the valve support 252, those skilled in the art would recognize that this is merely an example and not a limitation. In embodiments, the unconstrained diameters along the length of the valve support 252 may be oversized as compared corresponding unconstrained diameters of the valve support 204. In other embodiments only the unconstrained diameters of some portions of the valve support 252 may be oversized as compared to the unconstrained diameters of corresponding portions of the valve support 204. For example, and not by way of limitation, in some embodiments, the first and third diameter $D_{2i}$, $D_{2o}$ of the valve support 252 may be oversized as compared to the first and third diameters $D_i$, $D_o$ of the valve support 204. In other embodiments, only the second diameter $D_{2c}$ of the valve support 252 may be oversized as compared to the second diameter $D_c$ of the valve support 204. Any combination of oversizing may be utilized.

Similar to the second heart valve device 150 of the embodiment of FIGS. 1-6, the second heart valve device 250 of the embodiment of FIGS. 7-9 may include a skirt (not shown) coupled to the valve support 252. The skirt may be one or more layers of a graft material. The graft material of the skirt may be coupled to the valve support 252 to provide a more secure engagement between the second heart valve device 250 and the valve support 204 of the first heart valve device 201, and to prevent paravalvular leaks between the second heart valve device 250 and valve support 204 of the first heart valve device 201. The skirt may be formed from a suitable natural or biological graft material such as pericardium or another membranous tissue including, but not limited to intestinal submucosa. Alternatively, the skirt may be a low-porosity woven fabric, such as polyester, polyethylene terephthalate (PET), or polytetrafluoroethylene (PTFE), which creates a one-way fluid passage when attached to the frame.

Figure 12:
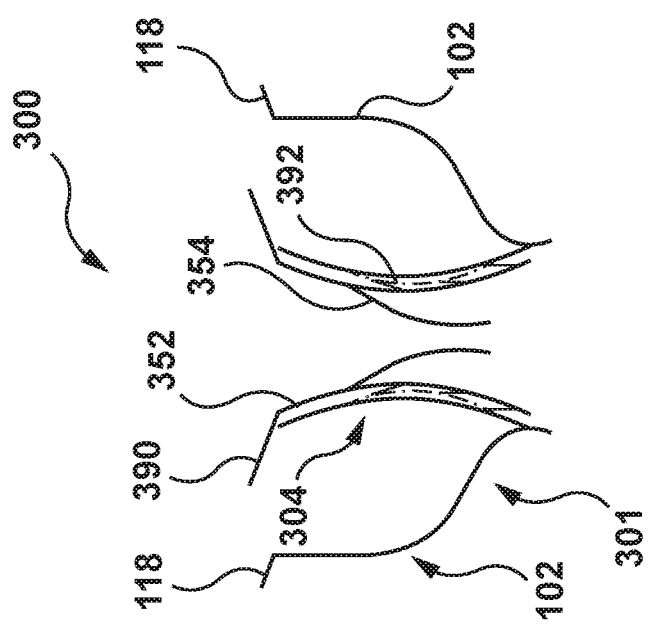
FIG. 12 depicts a schematic side view of the second heart valve device of FIG. 11 deployed within the first heart valve device of FIG. 10 to form a modular heart valve prosthesis according to an embodiment hereof.
Figure 11:
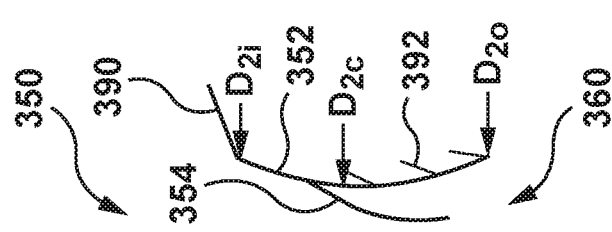
FIG. 11 depicts a schematic side view of a second heart valve device configured to be deployed within the first heart valve device of FIG. 10 to form a modular heart valve prosthesis.
Figure 10:
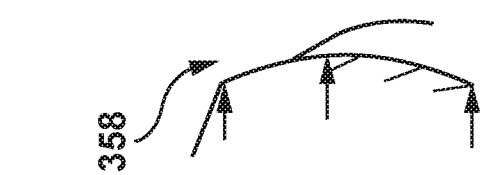
FIG. 10 depicts a schematic side view of a first heart valve device of a modular heart valve prosthesis according to an embodiment hereof.

FIGS. 10-12 schematically depict a modular heart valve prosthesis 300 according to another embodiment hereof. Similar to the modular heart valve prostheses 100 and 200, the modular heart valve prosthesis 300 includes a first heart valve device 301 and a second heart valve device 350 configured to be deployed within the first heart valve device 301, as shown in FIG. 12.

As shown in FIGS. 10 and 12, the first heart valve device 301 of the modular heart valve prosthesis 300 includes an anchoring member or frame 102 at least partially surrounding and coupled to a valve frame or support 304. The first heart valve device 301 further includes a first or temporary prosthetic valve 306 coupled to, mounted within, or otherwise carried by the valve support 304. The first heart valve device 301 is configured for placement within a native mitral valve and includes a downstream or distal end portion, referred to herein as an outflow portion 308, and an upstream or proximal end portion, referred to herein as an inflow portion 310.

The first heart valve device 301 identical to the first heart valve device 201 of FIG. 7-9, and thus need not be described in detail here. All of the description and variations noted above with respect to the first heart valve device 201 of FIG. 7-9, which includes the description and variations described with respect to the first heart valve device 101 of FIGS. 1-6, and in particular with respect to the anchoring member 102 of the first heart valve device 101, are incorporated into the description of the first heart valve device 301 of FIGS. 10 and 12. Thus, for example, and not by way of limitation, the anchoring member 102 of the first heart valve device 301 may include all of the details, descriptions, variations, and additional items described with respect to the anchoring member 102 of the modular heart valve prostheses 100, 200

(such as, but not limited to the brim 118, tissue engaging elements 114, graft material 112, sealing component 128, etc.). Further, all details of the valve support 204 described with respect to the first heart valve device 201 of FIGS. 7-9 are incorporated into the valve support 304 of the first heart valve device 301 of FIGS. 10-12. Thus, the valve support 304 is a generally hourglass shape with a first diameter $D_i$ at an inflow end thereof, a second diameter $D_c$ in a central portion thereof, and a third diameter $D_o$ at an outflow end thereof, wherein the first and third diameters $D_i$ and $D_o$ are larger than the second diameter $D_c$. The first heart valve device 301 further includes a temporary prosthetic valve 306 disposed within the interior of the valve support 304. The prosthetic valve 306 is as described above with respect to the prosthetic valves 106 and 206. Therefore, the details of the temporary prosthetic valve 306 will not be repeated.

In embodiments hereof, both the anchoring frame 102 and the valve support 304 of the first heart valve device 301 are self-expanding to return to a radially expanded state from a radially compressed state and may be made from materials such as, but not limited to stainless steel, a pseudo-elastic metal such as a nickel titanium alloy (e.g. NITINOL), or a so-called super alloy, which may have a base metal of nickel, cobalt, chromium, or other metal. "Self-expanding" as used herein means that a structure/component has a mechanical memory to return to the radially expanded configuration or state as described herein. Thus, the first heart valve device 301 has a radially compressed configuration for delivery within a delivery system and the radially expanded configuration for deployment within an annulus of the native heart valve site.

As previously described, the prosthetic valve 306 of the first heart valve device 301 is referred to as a temporary valve because the valve leaflets thereof are made of relatively thin material such that the first heart valve device 301 may be radially compressed to a smaller diameter or profile radially compressed configuration for delivery. Such a smaller diameter or profile is particularly useful for mitral valve prostheses because a transseptal approach to the native mitral valve requires a tight turning radius. A larger mitral valve prosthesis may have difficulty making the required turn in the radially compressed configuration. Thus, the valve leaflets of the temporary prosthetic valve 206 may be made of thin synthetic materials such as, but not limited to, polyester, polyethylene terephthalate (PET), polytetrafluoroethylene (PTFE), polyurethane, cloth materials, nylon blends, and polymeric materials. In a particular example, the valve leaflets 107 are formed of polyethylene terephthalate (PET) fabric. The valve leaflets have a thickness in the range of about 0.04 mm to about 0.10 mm. In an embodiment, the valve leaflets 107 have a thickness of approximately 0.07 mm. The valve leaflets are sutured or otherwise securely and sealingly attached to an inner circumference of the valve support 304 and/or a graft material (not shown) which encloses or lines the valve support 304.

As explained above, it is desirable for the first heart valve device 301 to have a small diameter or profile when in the radially compressed configuration. Therefore, as described above, the first heart valve device 301 includes a thin prosthetic valve 306 disposed within the valve support 304, approximately 0.07 mm in thickness. However, such a thin prosthetic valve 306 cannot serve as a long-term replacement valve for the native mitral valve due to limited durability of such a thin fabric prosthetic valve. However, the prosthetic valve 306 can serve as a temporary or short term valve.

Thus, as described in more detail below, the first heart valve device 301 with the temporary prosthetic valve 306 is delivered and deployed at the native mitral valve. The second heart valve device 350, as shown in FIGS. 11 and 12, is thereafter delivered and deployed within the valve support 304 of the first heart valve device 301 to form the modular heart valve prosthesis 300. The second heart valve device 350 is thus separate from the first heart valve device 301 until the second heart valve device 350 is delivered to and deployed within the already deployed first heart valve device 301.

The second heart valve device 350 shown in FIGS. 11 and 12 is identical to the second heart valve device 250 shown in FIGS. 8 and 9, except for additional features described below. Therefore, all of the details of the second heart valve device 250 are incorporated into the second heart valve device 350 and will not be repeated with respect to the second heart valve device 350. Therefore, for example and not by way of limitation, the second heart valve device 350 includes a valve support 352 and a second or permanent prosthetic valve 354 disposed within and coupled to the frame 352. The second heart valve device 350 also includes an inflow end 358 and an outflow end 360. The second heart valve device 350 may further include a skirt (not shown) coupled to the valve support 352.

The valve support 352 may be a stent or frame that supports the prosthetic valve 354 within the interior of the valve support 352. As described above with respect to the valve support 252, the valve support 352 may be any stent structure including components such as, but not limited to, struts, bends/crowns, longitudinal bars, and other structural features known to those skilled in the art. The valve support 352 of the second valve device 350 may be similar to the valve support 152 of the embodiment of FIGS. 1-6 except that the valve support 152 is generally cylindrical, as shown in FIG. 5, and the valve support 352 has a hourglass shape, as shown in FIGS. 11 and 12. Thus, as described above, the valve support 352 includes a first diameter $D_{2i}$ at the inflow end thereof, a second diameter $D_{2c}$ at a central portion thereof, and the third diameter $D_{2o}$ at the outflow end thereof, the first and third diameters $D_{2i}$, $D_{2o}$ being larger than the second diameter $D_{2c}$.

Thus, the valve support 352 of the second valve device 350 has a similar hourglass shape as the valve support 304 of the first heart valve device 301. The hourglass shape of each valve support 304/352 enables a more secure connection between the valve support 352 and the valve support 304 when the valve support 352 is deployed within the valve support 204, as shown in FIG. 12. The corresponding hourglass shapes enables the use of a self-expanding valve support 352 with less of a likelihood of the valve support 352 of the second heart valve device 350 moving or migrating after deployment within the valve support 304 than if the valve supports were cylindrical. Further, the valve support 352 of the second valve device 350 may be oversized with respect to the valve support 304 of the first valve device 301, as described above with respect to the valve support 252 and the valve support 204.

The second heart valve device 350 differs from the second heart valve device 250 in that the second heart valve device 350 includes a brim 390 extending radially outwardly from the inflow end 358 of the valve support 352 and barbs 392 extending radially outward from an outer surface of the valve support 352. Both the brim 390 and the barbs 392 enhance engagement between the second heart valve device 350 and the valve support 304 of the first heart valve device 301. Although the second heart valve device 350 of FIGS. 11 and 12 includes both the brim 390 and the barbs 392, it is not required that both be included. Therefore, the second heart valve device 350 can include the brim 390 and not the barbs 392, the barbs 392 and not the brim 390, both the brim 390 and the barbs 392, or neither the brim 390 nor the barbs 392 (in which case the second heart valve device 350 would be like the second heart valve device 250. Further, one of or both of the brim and the barbs described with respect to the second heart valve device 350 may be included in the second heart valve devices 150, 250, and 450.

The brim 390 extends radially outwardly from an inflow end of the valve support 352 when in a radially expanded configuration. The brim 390 may be a sinusoidal ring, such as one of the sinusoidal rings 120A, 120B of the anchoring member 102, or may be a pair of sinusoidal rings such as the sinusoidal rings 120A, 120B of the anchoring member. In other embodiments, the brim 390 may be a lattice of struts, or other structure formed of the same or similar material as the valve support 352. In embodiments, the brim 390 extends parallel to a central longitudinal axis of the valve support 352 when in a radially compressed configuration for delivery, and then extends radially outwardly at a 30 to 90 degree angle relative to the central longitudinal axis of the valve support 352 in a radially expanded or deployed configuration, as shown in FIGS. 11 and 12. When the second heart valve device 350 is deployed within the valve support 304 of the first heart valve device 301, as shown in FIG. 12, the brim 390 is disposed upstream of and extends radially outward of the upstream end of the valve support 304. In this manner, blood flow and other forces pushing the second heart valve device 350 in a downstream direction are opposed by the brim 390 contacting the upstream end of the valve support 304, thereby preventing downstream migration of the second heart valve device 350. Further, the brim 390 acts as a partial roof to the trough formed between an inner surface of the anchoring member 102 and an outer surface of the valve support 304, thereby reducing washout of blood from the trough. Encouraging stagnant blood in the trough accelerates filling of the trough, which stabilizes the assembled modular valve prosthesis 300.

The barbs 392 be struts that extend radially outward from an outer surface of the valve support 352. In the embodiment shown, there are three rows of barbs 392, however, more or fewer rows of barbs 392 may be included. Further the barbs 392 may be distributed around an outer circumference of the valve support 352, either equally spaced around the circumference or asymmetrically distributed around the circumference. In other embodiments, the barbs 390 may be distributed around only a portion of the circumference of the valve support 352. A first end of each barb 392 is coupled to the valve support and a second end of each barb 392 is a free end. The free end of each barb 392 may include a sharp tip. The barbs 392 may be separate items attached to the valve support 352 or may be formed unitarily with the valve support 352. In embodiments, the barbs 392 are parallel to the central longitudinal axis of the valve support 352 when in a radially compressed configuration and extend radially outward and in an upstream direction in a radially expanded configuration at an angle of 15 to 75 degrees from the central longitudinal axis, as shown in FIGS. 11 and 12. When the second heart valve device 350 is deployed within the valve support 304 of the first heart valve device 301, as shown in FIG. 12, the barbs 392 of the second heart valve device 350 engage the valve support 304, and depending on the location of the barbs 392 relative to the valve support 304, may extend through the temporary prosthetic valve 306 of the valve support 304 and any graft material covering the valve support 304. In embodiments, due to the barbs 392 being angled in the upstream direction and engaged with the valve support 304, forces acting on the second heart valve device 350 in an upstream direction are opposed by the barbs' 392 engagement with the valve support 304, thereby minimizing migration in the upstream direction. The barbs 392 may be made of the same or similar material as the valve support 352.

Figure 15:
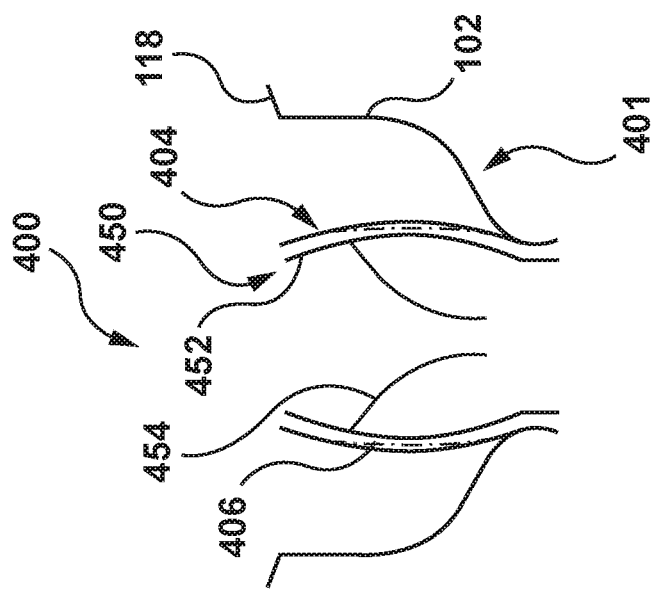
FIG. 15 depicts a schematic side view of the second heart valve device of FIG. 14 deployed within the first heart valve device of FIG. 13 to form a modular heart valve prosthesis according to an embodiment hereof.
Figure 14:
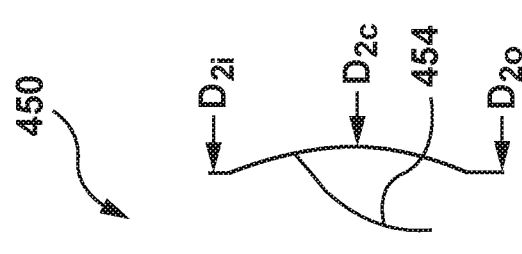
FIG. 14 depicts a schematic side view of a second heart valve device configured to be deployed within the first heart valve device of FIG. 13 to form a modular heart valve prosthesis.
Figure 13:
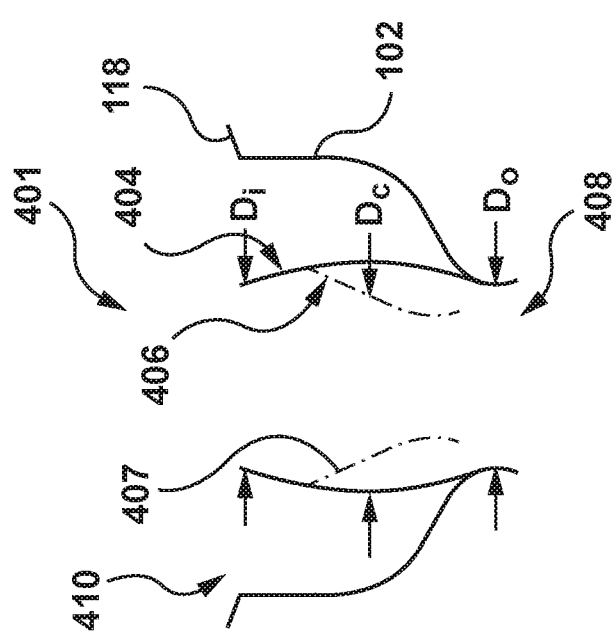
FIG. 13 depicts a schematic side view of a first heart valve device of a modular heart valve prosthesis according to an embodiment hereof.

FIGS. 13-15 schematically depict a modular heart valve prosthesis 400 according to another embodiment hereof. Similar to the modular heart valve prostheses 100, 200, and 300, the modular heart valve prosthesis 400 includes a first heart valve device 401 and a second heart valve device 450 configured to be deployed within the first heart valve device 401, as shown in FIG. 15.

As shown in FIGS. 13 and 15, the first heart valve device 401 of the modular heart valve prosthesis 400 includes an anchoring member or frame 102 at least partially surrounding and coupled to a valve frame or support 404. The first heart valve device 401 further includes a first or temporary prosthetic valve 406 coupled to, mounted within, or otherwise carried by the valve support 404. The first heart valve device 401 is configured for placement within a native mitral valve and includes a downstream or distal end portion, referred to herein as an outflow portion 408, and an upstream or proximal end portion, referred to herein as an inflow portion 410.

The anchoring member 102 of the first heart valve device 401 is numbered the same as the anchoring member 102 of the first heart valve device of 101 of the modular heart valve prosthesis 100 because it is substantially the same as the anchoring member 102 of the first heart valve device 101. Therefore, the detailed description thereof will not be repeated for the first heart valve device 401 of the modular heart valve prosthesis 400, and all details, descriptions, variations, and additional items described with respect to the anchoring member 102 of the first heart valve device 101 of the modular heart valve prosthesis 100 (such as, but not limited to the brim 118, tissue engaging elements 114, graft material 112, sealing component 128, etc.) may be included and incorporated in the anchoring member 102 of the first heart valve device 401 of the modular heart valve prosthesis 400.

Figure 6:
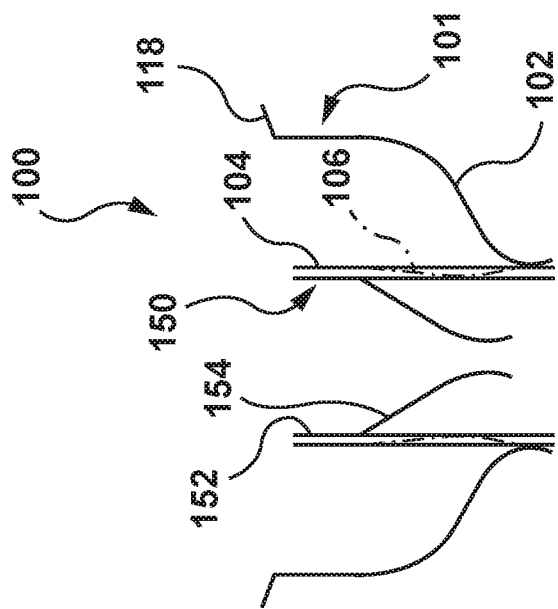
FIG. 6 depicts a schematic side view of the modular heat valve prosthesis of FIG. 1 with the second heart valve device deployed within the first heart valve device.

The valve support 404 of the first heart valve device 401 of the modular heart valve prosthesis 400 may be a generally tubular frame or stent that supports the temporary prosthetic valve 406 within the interior of the valve support 404. In some embodiments, the valve support 404 may be any structure of a stent, including longitudinal posts, circumferential struts and crowns, and other structural features known to those skilled in the art. The valve support 404 may be similar in structure to the valve support 404, except for the shape thereof. In particular, as can be seen in FIGS. 4 and 6, the valve support 104 is generally cylindrical, whereas, as can be seen in FIGS. 13 and 15, the valve support 404 is generally reverse hourglass or biconic in shape. In particular, the valve support 404 includes a first diameter $D_i$ at an inflow end thereof, a second diameter $D_c$ in a central portion thereof, and a third diameter $D_o$ at an outflow end thereof, wherein the first and third diameters $D_i$ and $D_o$ are smaller than the second diameter $D_c$.

In embodiments hereof, both the anchoring frame 102 and the valve support 404 of the first heart valve device 401 are self-expanding to return to a radially expanded state from a radially compressed state and may be made from materials such as, but not limited to stainless steel, a pseudo-elastic metal such as a nickel titanium alloy (e.g. NITINOL), or a so-called super alloy, which may have a base metal of nickel, cobalt, chromium, or other metal. "Self-expanding" as used herein means that a structure/component has a mechanical memory to return to the radially expanded configuration or state as described herein. Thus, the first heart valve device 401 has a radially compressed configuration for delivery within a delivery system and the radially expanded configuration for deployment within an annulus of the native heart valve site.

As previously described, the first heart valve device 401 includes the temporary prosthetic valve 406 within the interior of the valve support 404. The temporary prosthetic valve 406 is configured as a one-way valve to allow blood flow in one direction and thereby regulate blood flow therethrough. The temporary prosthetic valve 406 is capable of blocking flow in one direction to regulate flow therethrough via valve leaflets 407 that may form a bicuspid or tricuspid replacement valve. The temporary prosthetic valve 406 is referred to as a temporary valve because the valve leaflets are made of relatively thin material such that the first heart valve device 401 may be radially compressed to a smaller diameter or profile radially compressed configuration for delivery. Such a smaller diameter or profile is particularly useful for mitral valve prostheses because a transseptal approach to the native mitral valve requires a tight turning radius. A larger mitral valve prosthesis may have difficulty making the required turn in the radially compressed configuration. Thus, the valve leaflets 407 of the temporary prosthetic valve 406 may be made of thin synthetic materials such as, but not limited to, polyester, polyethylene terephthalate (PET), polytetrafluoroethylene (PTFE), polyurethane, cloth materials, nylon blends, and polymeric materials. In a particular example, the valve leaflets 407 are formed of polyethylene terephthalate (PET) fabric. The valve leaflets have a thickness in the range of about 0.04 mm to about 0.10 mm. In an embodiment, the valve leaflets 107 have a thickness of approximately 0.07 mm. The valve leaflets 407 are sutured or otherwise securely and sealingly attached to an inner circumference of the valve support 404 and/or a graft material (not shown) which encloses or lines the valve support 404.

As noted above, it is desirable for the first heart valve device 401 to have a small diameter or profile when in the radially compressed configuration. Therefore, as described above, the first heart valve device 401 includes a thin prosthetic valve 406 disposed within the valve support 404, approximately 0.07 mm in thickness. However, such a thin prosthetic valve 406 cannot serve as a long-term replacement valve for the native mitral valve due to limited durability of such a thin fabric prosthetic valve. However, the prosthetic valve 406 can serve as a temporary or short term valve.

Thus, as described in more detail below, the first heart valve device 401 with the temporary prosthetic valve 406 is delivered and deployed at the native mitral valve. The second heart valve device 450, as shown in FIGS. 14 and 15, is thereafter delivered and deployed within the valve support 404 of the first heart valve device 401 to form the modular heart valve prosthesis 400. The second heart valve device 450 is thus separate from the first heart valve device 401 until the second heart valve device 450 is delivered to and deployed within the already deployed first heart valve device 401.

The second heart valve device 450 may be generally tubular. The second heart valve device 450 includes a valve support or frame 452 and a second or permanent prosthetic valve 454 disposed within and coupled to the frame 452. The second heart valve device 450 includes an inflow end 458 and an outflow end 460. The second heart valve device 450 may further include a skirt (not shown) coupled to the valve support 452.

The valve support 452 may be a stent or frame that supports the prosthetic valve 454 within the interior of the valve support 452. The valve support 452 may be any stent structure including components such as, but not limited to, struts, bends/crowns, longitudinal bars, and other structural features known to those skilled in the art. The valve support 452 of the second valve device 450 may be similar to the valve support 452 of the embodiment of FIGS. 1-6 except that the valve support 452 is generally cylindrical, as shown in FIG. 5, and the valve support 452 has a reverse hourglass or biconic shape, as shown in FIGS. 14 and 15. Thus, the valve support 452 includes a first diameter $D_{2i}$ at the inflow end thereof, and second diameter $D_{2c}$ at a central portion thereof, and the third diameter $D_{2o}$ at the outflow end thereof, the first and third diameters $D_{2i}$, $D_{2o}$ being smaller than the second diameter $D_{2c}$.

Thus, the valve support 452 of the second valve device 450 has a similar reverse hourglass shape as the valve support 404 of the first heart valve device 401. The reverse hourglass shape of each valve support 404/452 enables a more secure engagement between the valve support 452 and the valve support 404 when the valve support 452 is deployed within the valve support 404, as shown in FIG. 15. The corresponding reverse hourglass shapes enables the use of a self-expanding valve support 452 with less of a likelihood of the valve support 452 of the second heart valve device 450 moving or migrating after deployment within the valve support 404 than if the valve supports were cylindrical.

Further, although not shown in FIGS. 14 and 15, the valve support 452 may also include a brim and/or barbs similar to the brim 390 and barbs 392 described above with respect to the valve support 352.

To further enhance the engagement between the valve support 452 and the valve support 404 when both are self-expanding, the valve support 452 of the second heart valve device 450 may be oversized with respect to the valve support 404 of the first heart valve device 401. Oversizing the valve support 452 of the second heart valve device 450 relative to the valve support 404 of the first heart valve device 401 is described in detail above with respect the valve support 252 of the second heart valve device 250 relative to the valve support 204 of the first heart valve device 201 of the modular heart valve prosthesis 200. Therefore, that description is incorporated into the description of oversizing the valve support 452 relative to the valve support 401 of the modular heart valve prosthesis 400.

Similar to the second heart valve device 150 of the embodiment of FIGS. 1-6, the second heart valve device 450 of the embodiment of FIGS. 13-15 may include a skirt (not shown) coupled to the valve support 452. The skirt may be one or more layers of a graft material. The graft material of the skirt may be coupled to the valve support 452 to provide a more secure engagement between the second heart valve device 450 and the valve support 404 of the first heart valve device 401, and to prevent paravalvular leaks between the second heart valve device 450 and valve support 404 of the first heart valve device 401. The skirt may be formed from a suitable natural or biological graft material such as pericardium or another membranous tissue including, but not limited to intestinal submucosa. Alternatively, the skirt may be a low-porosity woven fabric, such as polyester, polyethylene terephthalate (PET), or polytetrafluoroethylene (PTFE), which creates a one-way fluid passage when attached to the frame.

The delivery and deployment of the modular heart valve prostheses disclosed herein will now be described with respect to FIGS. 16-24. FIGS. 16-24 are sectional cut-away views of a heart HE illustrating a trans-septal method approach for delivering and deploying the modular heart valve prosthesis 100. Although FIGS. 16-24 show delivery and deployment the modular heart valve prosthesis 100, the same method can be used for delivering and deploying the modular heart valve prostheses 200, 300, or 400.

FIGS. 16-20 show a delivery system 500 for delivering and deploying the first heart valve device 101 of the modular heart valve prosthesis 100. The delivery system 500 shown in schematically in FIGS. 16-20 can be any delivery system capable of percutaneously delivering the first heart valve device 101 to the location of a native mitral valve. Therefore, any details described with respect to the delivery system 500 are examples only and not meant to be limiting. Further details of the particular delivery system 500 may also be found in U.S. patent application Ser. No. 16/807,010, filed Mar. 2, 2020, the contents of which are incorporated by reference herein in their entirety. It is understood that other delivery systems may be used to deliver and deploy the first heart valve device 101 and the second heart valve device 150.

Figure 16:
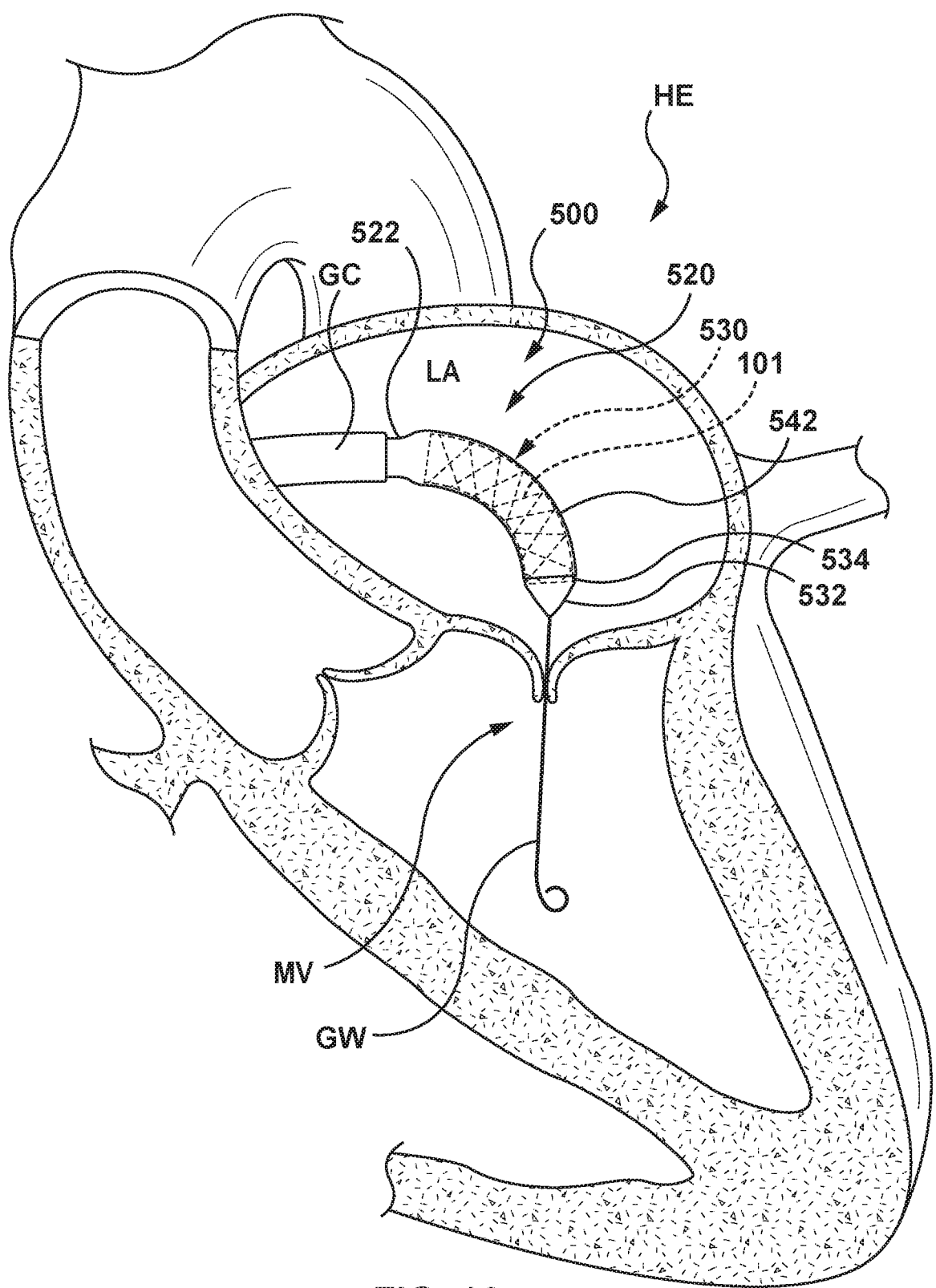
FIGS. 16-20 depict schematically a method for delivering and deploying of a first heart valve device side view of a first heart valve device of a modular heart valve prosthesis according to an embodiment hereof.

With reference to FIG. 16, the delivery system 500 is shown after having been introduced into the vasculature via a percutaneous entry point technique, such as the Seldinger technique, and having been tracked through the vasculature and into the left atrium LA so that a distal tip component 532 is positioned proximate the native mitral valve MV. Intravascular access to the right atrium may be achieved via a percutaneous access site to femoral vein, into the common iliac vein, through the inferior vena cava, and into the right atrium, or other known access routes as described in the background above. A guidewire GW is advanced via the route and is directed into the right atrium. The guidewire GW traverses the right atrium and traverses through the atrial septum with the aid of a trans-septal needle or a pre-existing hole, thereby entering the left atrium LA. Once the guidewire GW is positioned, the percutaneous entry point and the trans-septal puncture are dilated to permit entry of a guide catheter GC into the left atrium LA. Thereafter, a delivery catheter 520 is advanced over the guidewire GW and through the guide catheter GC into the left atrium LA through the punctured atrial septum and positioned proximate or upstream to the native mitral valve MV. Although described as a transfemoral antegrade approach for percutaneously accessing the mitral valve, the first heart valve device 101 may be positioned within the desired area of the heart via other different entry methods such as a trans-septal antegrade approach via a thoracotomy for accessing the mitral valve. In addition, although described with the use of the guide catheter GC and the guidewire GW, in other embodiments the delivery catheter 520 may access the right atrium without the use of a guidewire and/or a guide catheter.

In FIG. 16, the distal portion of the delivery system 500 is shown positioned in the left atrium LA with a capsule portion 530, including a capsule segment 542 of an outer shaft 522 and a distal shaft component 534 of the distal tip component 532 in combination holding the first heart valve device 101 in a radially compressed configuration. With additional reference to FIG. 16, and as will be understood by those knowledgeable in the pertinent art, the delivery catheter 520 includes other features such as, but not limited to, a handle, proximal shaft portion, and other catheter elements know to those skilled in the art. Further, some of the elements, such as but not limited to, the handle and some length of a proximal segment of the delivery catheter 520, are exposed externally of the patient for access by a clinician, even as the first heart valve device 101 has been advanced fully to the desired treatment site (e.g., left atrium LA) in the patient. By manipulating the handle of the delivery catheter 520 from outside the vasculature, a clinician may advance, retract, and remotely manipulate and steer the distal portion of the delivery catheter 520 through the sometimes tortuous intravascular path.

Figure 17:
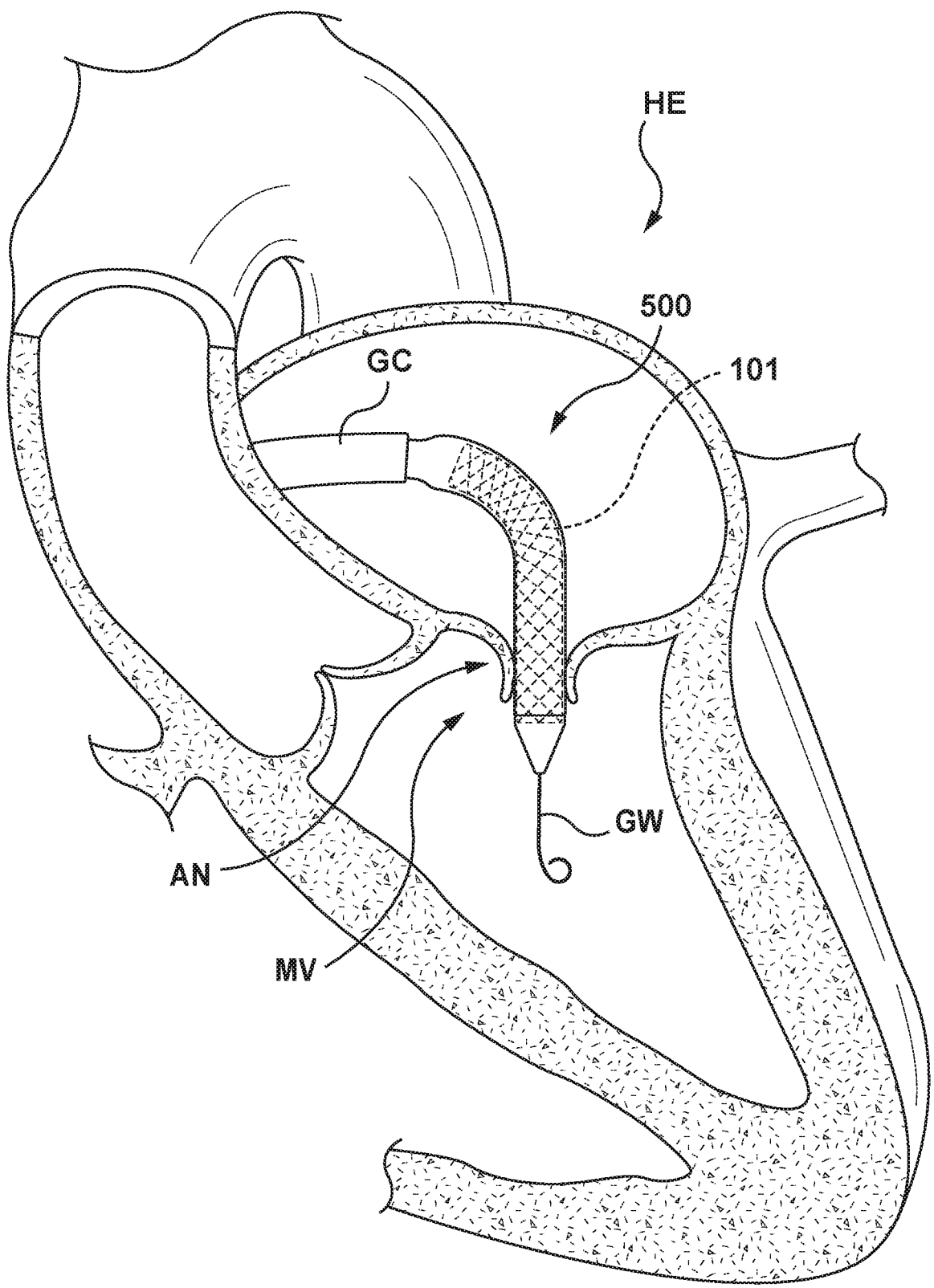

In a next delivery step shown in FIG. 17, the delivery catheter 520 is advanced into proximity to and/or apposition within the annulus AN and/or leaflets of the native mitral valve MV. The delivery catheter 520 is advanced until the first heart valve device 101 in the radially compressed configuration is centered at the native mitral valve MV.

Figure 18:
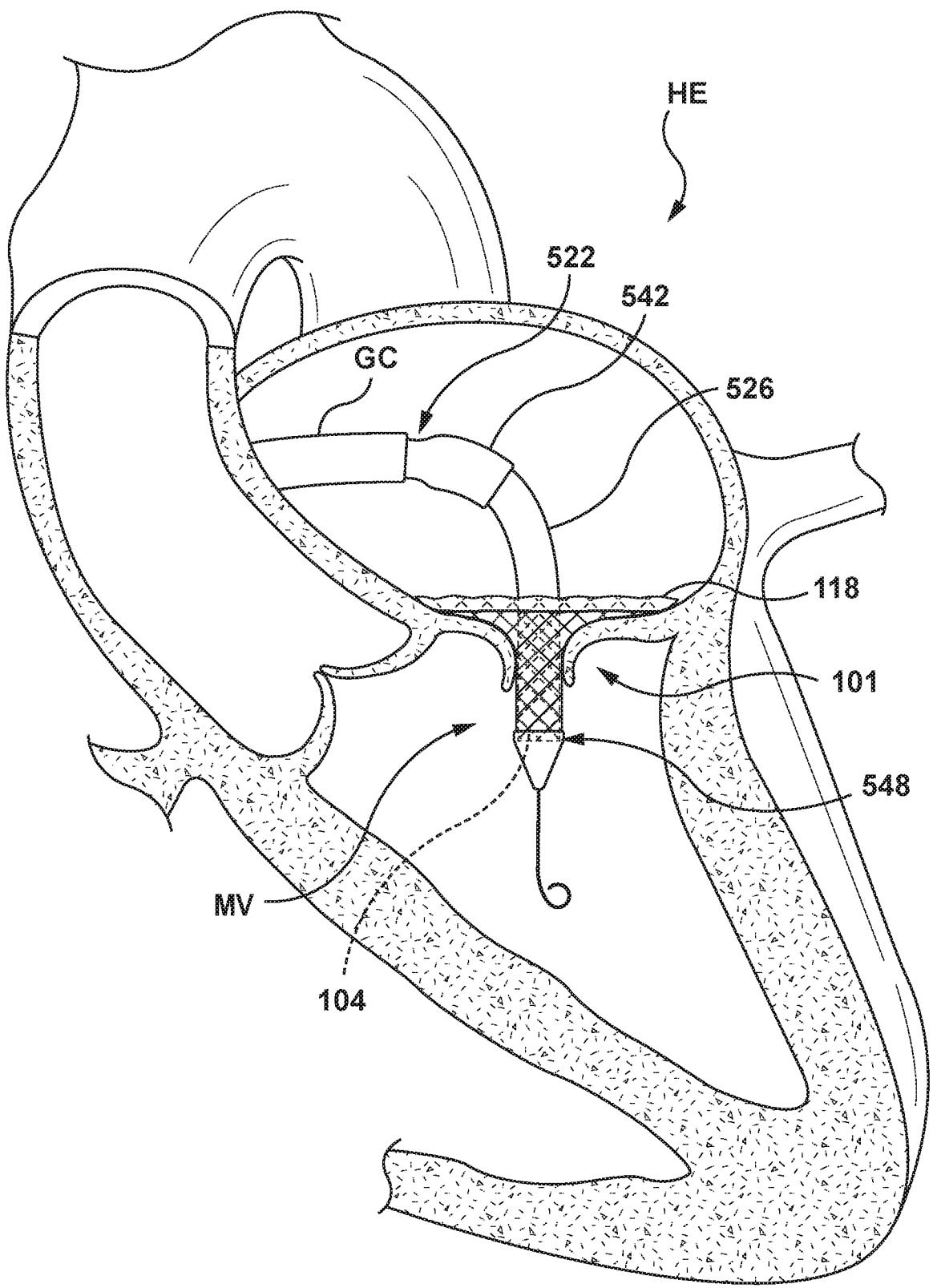

Once the delivery catheter 520 is position such that the first heart valve device 101 is positioned within the native mitral valve MV, an actuator of the catheter 520 may be actuated to proximally retract the outer shaft 522, as shown in FIG. 18. Proximal retraction of the outer shaft 522 causes the capsule segment 542 of the outer shaft 522 to be proximally retracted such that the capsule segment 542 does not encircle or retain the anchoring member 102 of the first heart valve device 101 (which includes at least the brim 118 of the first heart valve device 101). Proximal retraction of the capsule segment 542 exposes and releases the anchoring member 102 of the first heart valve device, thereby enabling at least the brim 118 of the anchoring member 102 to radially expand, as shown in FIG. 18. In addition to radial expansion of the brim 118, the remainder of the anchoring member 102 is also released from the capsule segment 242 and radially expands relative to the inner valve support 104, which remains radially compressed within a capsule segment 548 of an intermediate shaft 526. Retraction of the capsule segment 542 and subsequent deployment of the anchoring member 102 may be considered a first stage of deployment of a deployment process for the first heart valve device 101. After proximal retraction of the capsule segment 542, the capsule segment 548 of the intermediate shaft 526 maintains the valve support 104 in the radially compressed state and the distal shaft component 534 of the distal tip component 532 maintains a distal portion of the first heart valve device 101 in the radially compressed state.

With the anchoring member 102 released from the capsule segment 542 of the outer shaft 522, the delivery catheter 520 in some embodiments may be manipulated to properly seat the first heart valve prosthesis device 101. For example, and not by way of limitation, the delivery catheter 520 may be pushed distally such that the brim 118 of the anchoring member 102 seats against the atrial side of the mitral valve annulus AN.

Figure 19:
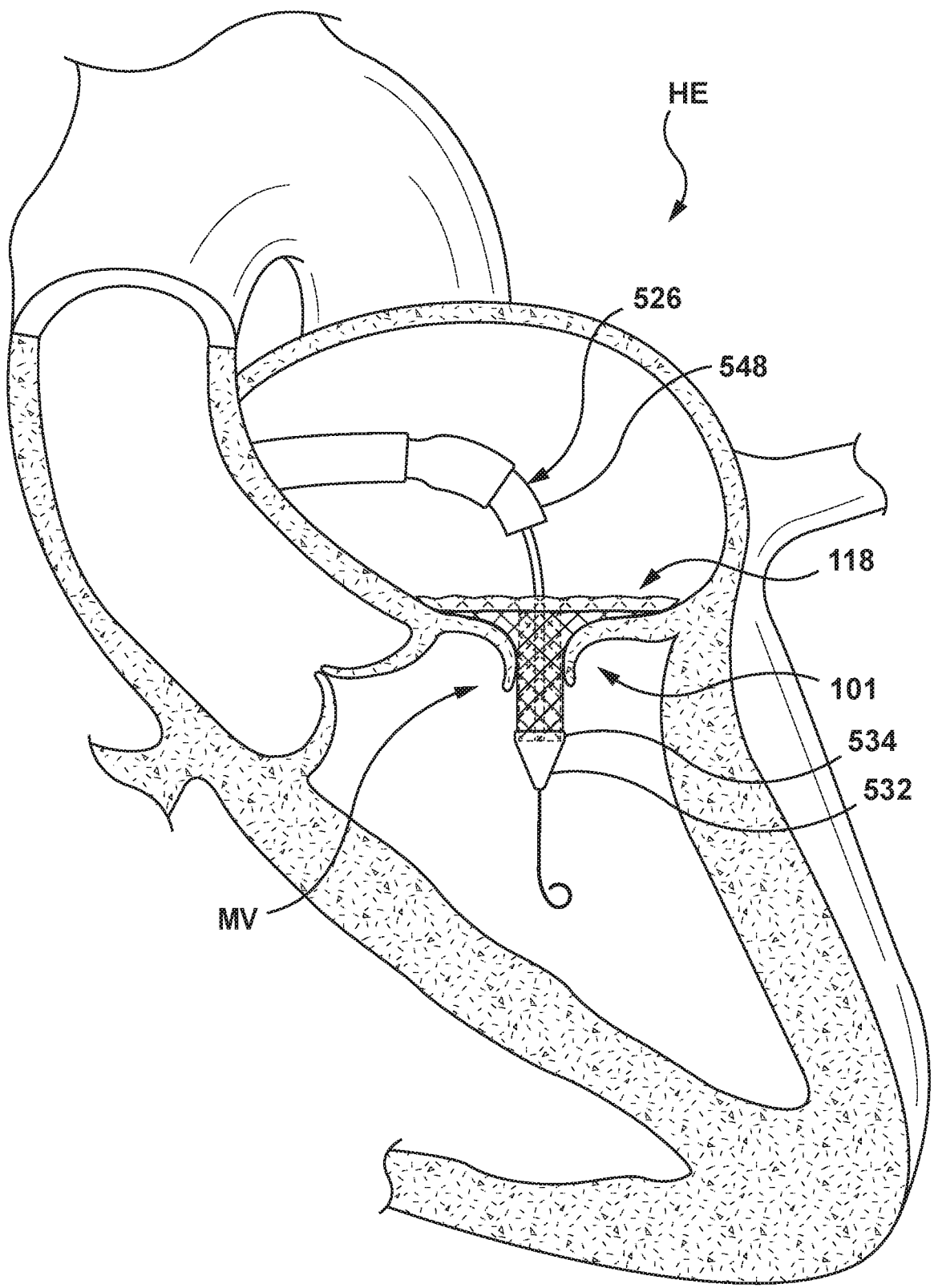

With reference to FIG. 19, once the first heart valve device 101 is properly positioned and the anchoring member 102 has been released from the capsule segment 542, an actuator of the catheter 520 may be actuated to proximally retract the intermediate shaft 526. The intermediate shaft 526 is retracted proximally such that a capsule segment 548 of the intermediate shaft 526 is retracted proximally such that the valve support 104 of the first heart valve device 101 is no longer retained within the capsule segment 548. Accordingly, the valve support 104 radially expands to the radially expanded state. Retraction of the capsule segment 548 and subsequent deployment of the valve support 104 may be considered a second stage of the deployment process for the first heart valve device 101. After proximal retraction of the capsule segment 548, the distal shaft component 534 of the distal tip component 532 maintains the distal portion of the heart valve device 101 in the radially compressed state.

Figure 20:
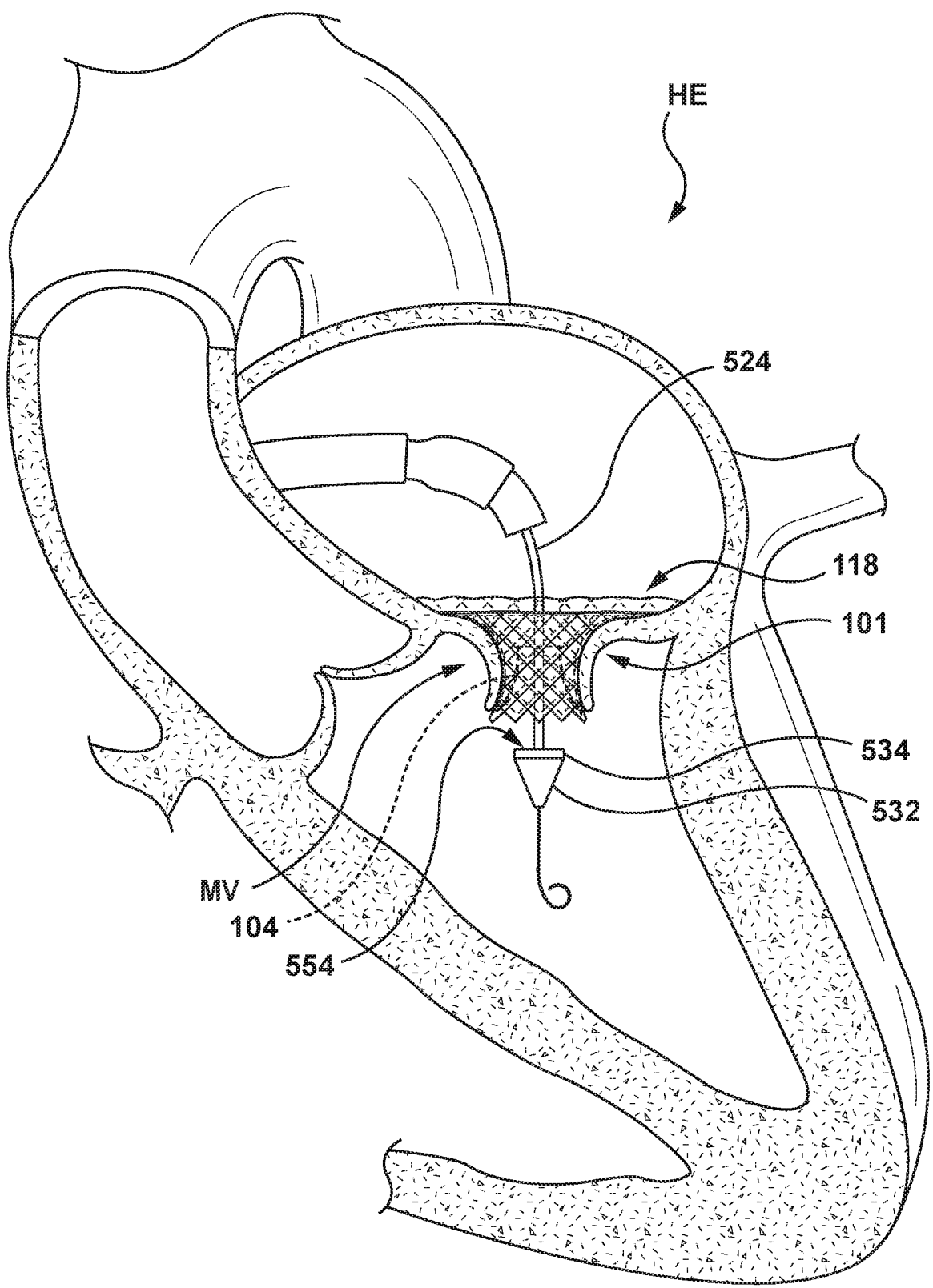

Referring next to FIG. 20, once the anchoring member 102 and the inner valve support 104 are each positioned and deployed within the native mitral valve MV, an actuator of the delivery catheter 520 may be actuated such that an inner shaft 524 is advanced in a distal direction. The inner shaft 524 is advanced distally such that the distal shaft component 534 of the distal tip component 532 is also advanced distally to uncover or release the distal or outflow portion of the first heart valve device 101, thereby enabling the outflow portion of the first heart valve device 101 to return to a radially expanded state within the native mitral valve MV. Further, release of the outflow portion of the first heart valve device 101 enables complete expansion of the anchoring member 102 and the valve support 104 to the radially expanded state.

Figure 21:
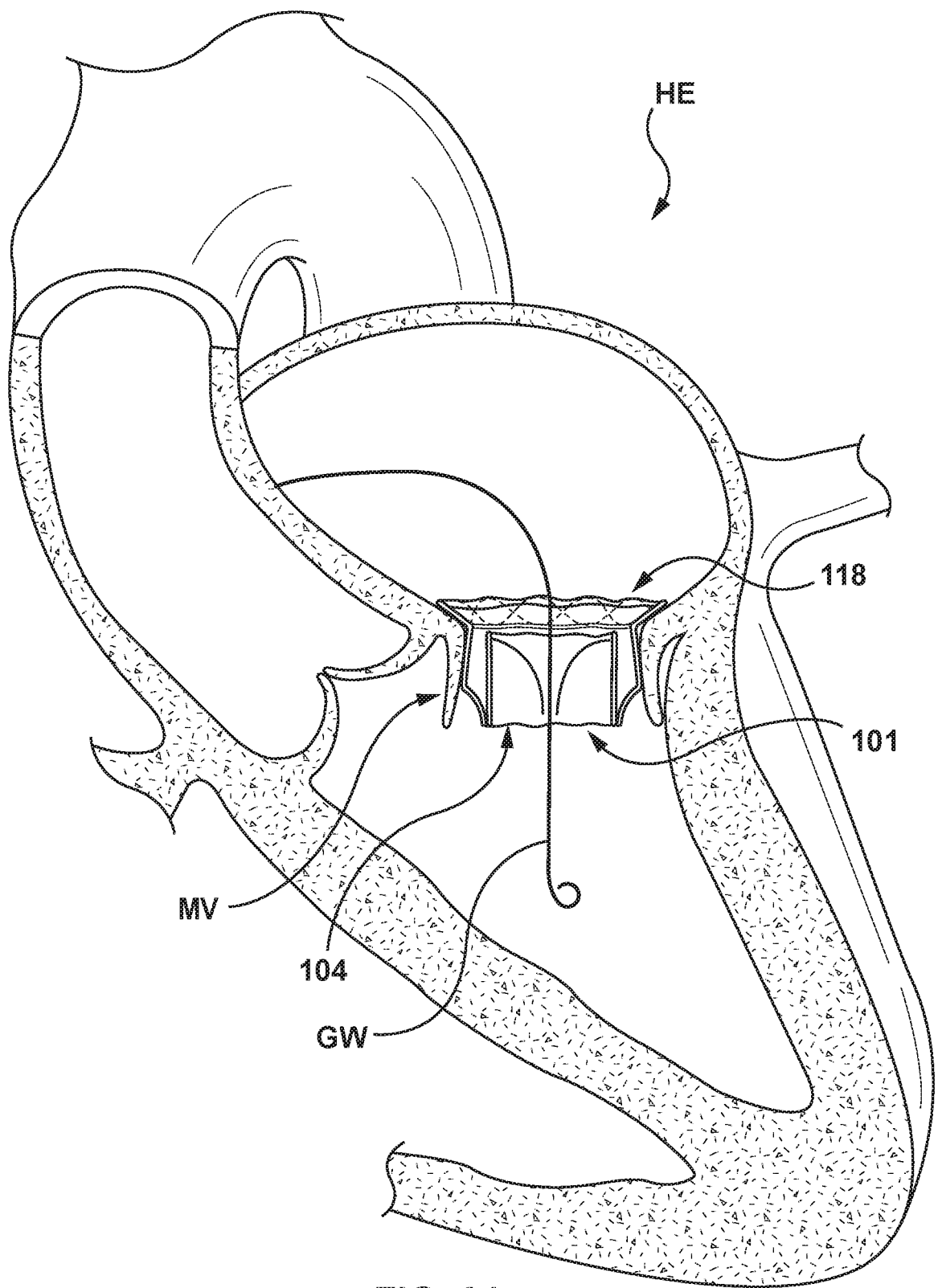
FIGS. 21-24 depict schematically for delivering and deploying a second heart valve device within the first heart valve device to form the modular heart valve prosthesis.

Following delivery, placement and implantation of first heart valve device 101 within the mitral valve MV (or other desired valve location), the delivery catheter 520 of the delivery system 500 is removed from the heart and out of the body of the patient, as would be understood by one of skill in the art. The deployed first heart valve device 101 with the delivery catheter 520 removed (but the guidewire GW remaining in place) is shown in FIG. 21.

Figure 22:
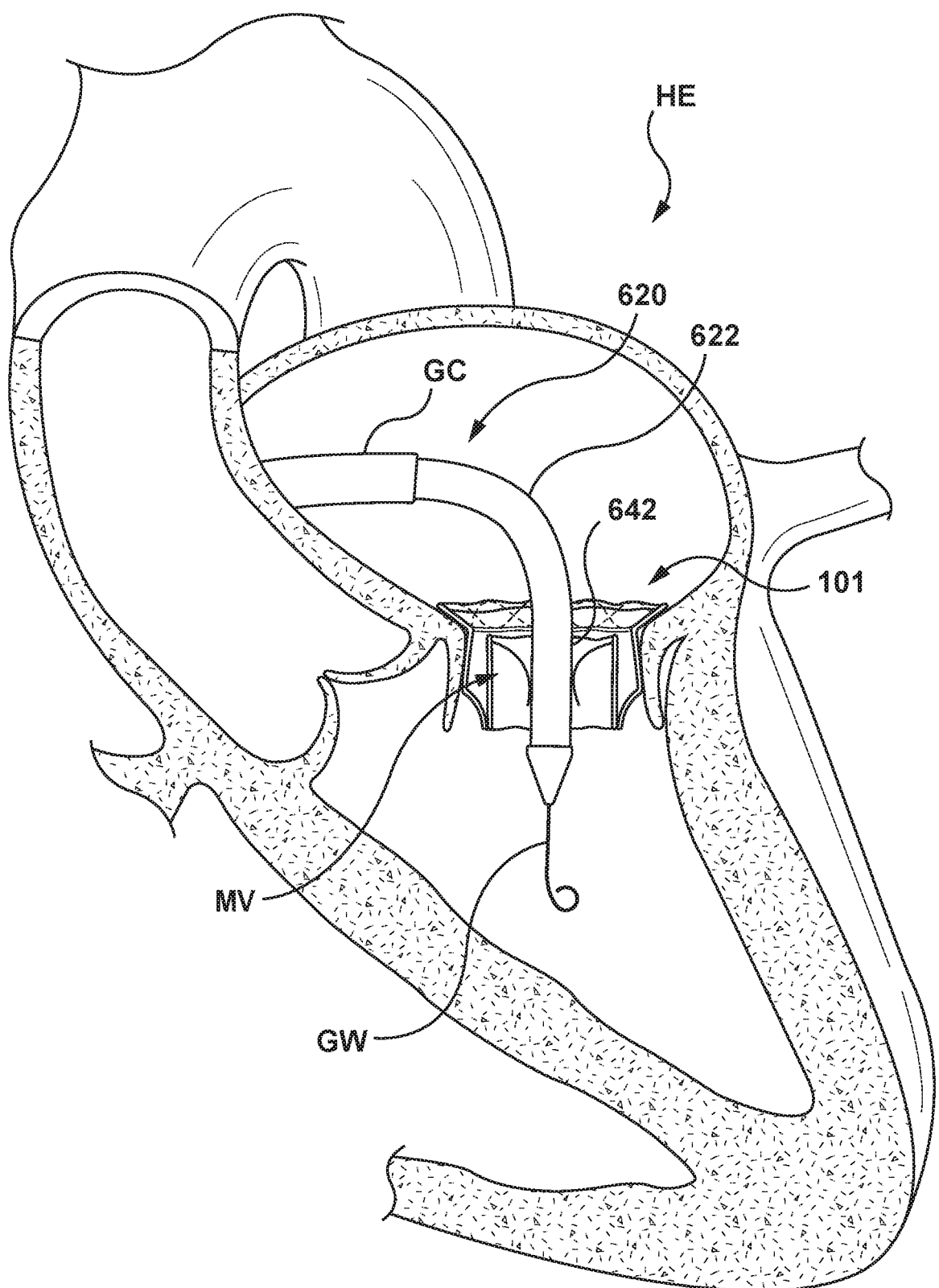

After delivery and deployment of the first heart valve device 101, a second delivery catheter 620 with the second heart valve device 150 disposed within a capsule 642 of an outer shaft 622 thereof is delivered to within the valve support 104 of the first heart valve device, as shown in FIG. 22. During the time it takes to remove the first delivery catheter 520 from the vasculature, and insert and track the second delivery catheter 620 the native mitral valve, the temporary prosthetic valve 106 of the first heart valve device 101 operates to maintain blood flow control through the mitral valve. Although the description of FIGS. 21-24 describes delivering and deploying the second heart valve device 150, it is understood that the method may apply equally to the second heart valve devices 250, 350, and 450. Further, as described in FIGS. 21-24, the second heart valve device is self-expanding. However, a balloon-expandable second heart valve device 150 may be used. Using a balloon-expandable second heart valve device 150, the second delivery catheter will be a balloon catheter, as known to those skilled in the art.

Figure 23:
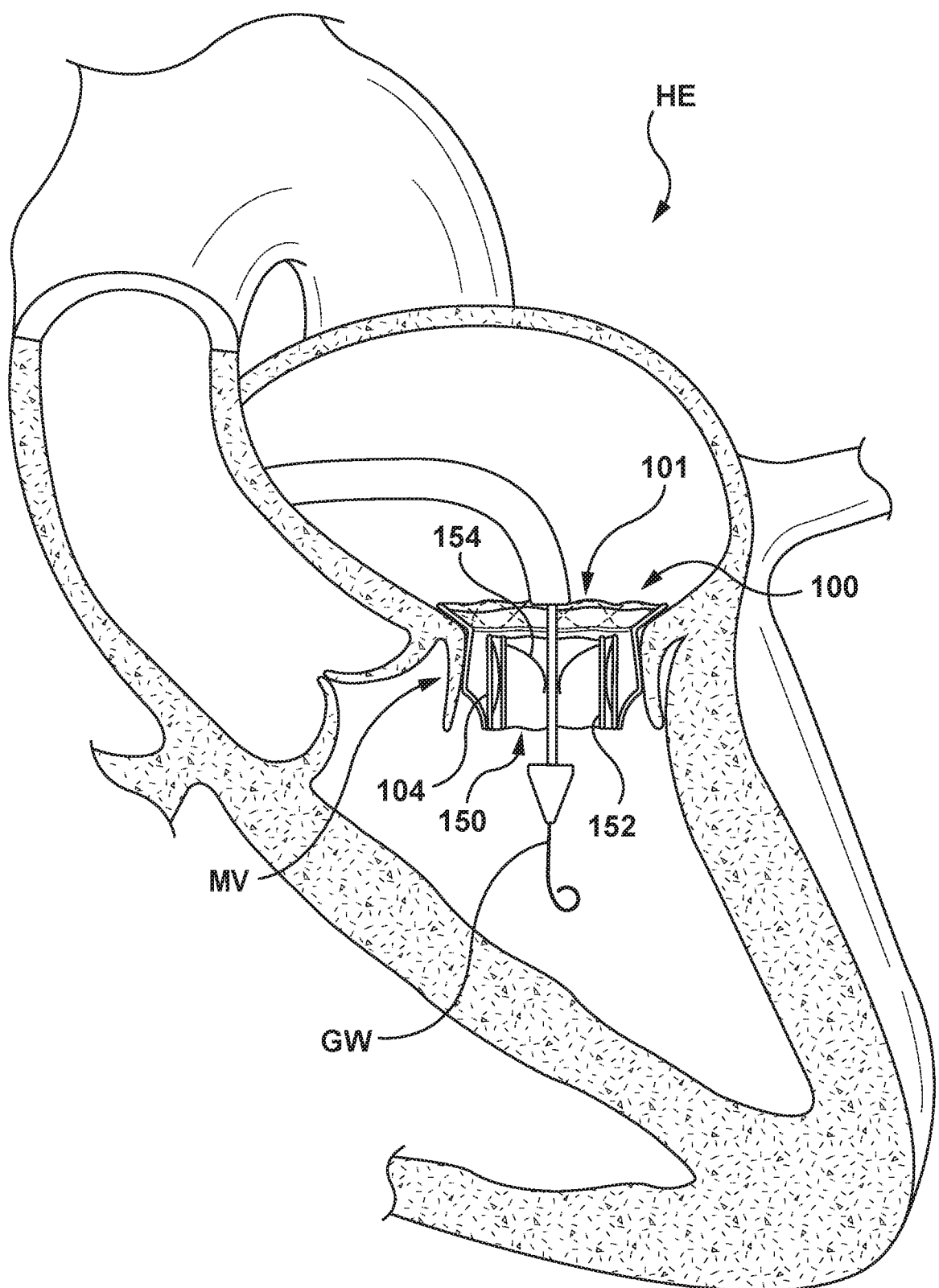

With the second delivery catheter 620 at the desired location, the capsule 642 is retracted proximally by retracting the outer shaft 622, thereby exposing the second heart valve device 150 and enabling the second heart valve device 150 to self-expand to the radially expanded configuration, as shown in FIG. 23. Those skilled in the art would understand that if the second heart valve device 150 is balloon expandable, this step of the method would comprise delivering inflation fluid to within a balloon of a balloon catheter, thereby radially expanding the balloon and the second heart valve device disposed thereon.

Figure 24:
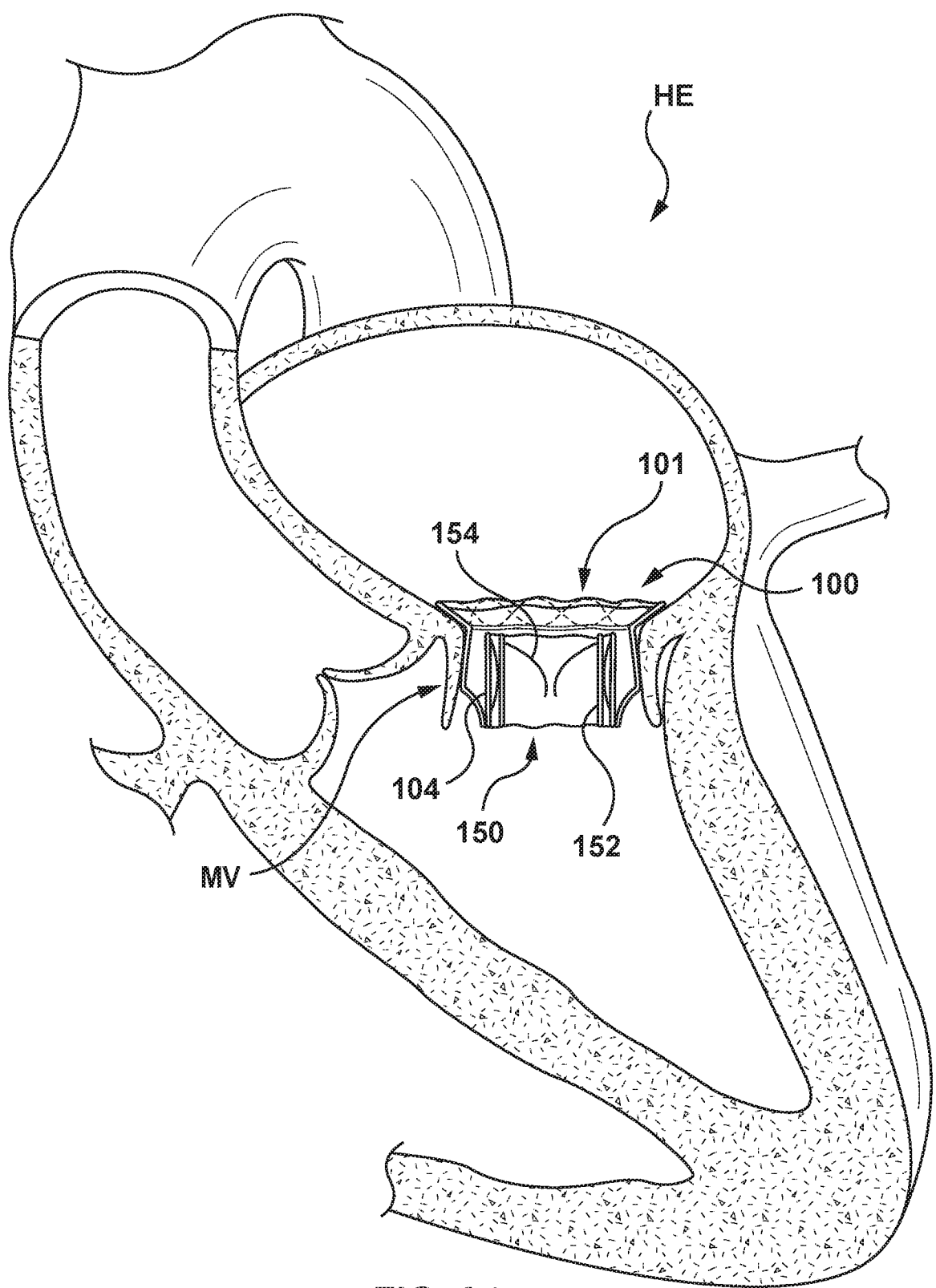

With the second heart valve device 150 radially expanded within the valve support 104 of the first heart valve device 101, the second delivery catheter 620 and the guidewire GW may be removed from the patient, thereby leaving the modular heart valve prosthesis 100 deployed within the mitral valve MV, as shown in FIG. 24.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments but should be defined only in accordance with the appended claims and their equivalents. It will also be understood that each feature of each embodiment discussed herein can be used in combination with the features of any other embodiment.

What is claimed:

1. A modular heart valve prosthesis comprising:
   a first heart valve device including,
      a first valve support including a first prosthetic valve disposed within the valve support, the first prosthetic valve comprising synthetic fabric leaflets having a first thickness, and
      an anchoring frame surrounding the first valve support and coupled to the first valve support, the anchoring frame including a first portion and a second portion; and
   a second heart valve device including a second valve support and a second prosthetic valve disposed within the second valve support, the second prosthetic valve comprising tissue leaflets having a second thickness, wherein the second thickness is greater than the first thickness,
      wherein in a first configuration the second heart valve device is separate from the first heart valve device and in a second configuration the second heart valve device is disposed within the first valve support of the first heart valve device.

2. The modular heart valve prosthesis of claim 1, wherein the first heart valve device is self-expanding, and wherein the second heart valve device is balloon expandable.

3. The modular valve prosthesis of claim 1, wherein the first heart valve device is self-expanding, and wherein the second heart valve device is self-expanding.

4. The modular heart valve prosthesis of claim 1, wherein the synthetic fabric leaflets of the first prosthetic valve are formed from material selected from the group consisting of polyester, polyethylene terephthalate (PET, e.g. DACRON), polytetrafluoroethylene (PTFE), polyurethane, cloth materials, nylon blends, and polymeric materials.

5. The modular heart valve prosthesis of claim 1, wherein the tissue leaflets of the second prosthetic valve are formed from material selected from the group consisting of bovine pericardium tissue and porcine pericardium tissue.

6. The modular valve prosthesis of claim 1, wherein the first thickness is in a range of about 0.04 mm to about 0.10 mm.

7. The modular heart valve prosthesis of claim 6, wherein the first thickness is about 0.07 mm.

8. The modular heart valve prosthesis of claim 1, wherein the second thickness is in the range of about 0.35 mm to about 0.5 mm.

9. The modular heart valve prosthesis of claim 1, wherein the first heart valve device has a crimped diameter of approximately 27 Fr.

10. The modular heart valve prosthesis of claim 9, wherein the second heart valve device has a crimped diameter of approximately 14 Fr.

11. The modular heart valve prosthesis of claim 1, wherein the first valve support and the second valve support are both generally cylindrical.

12. The modular valve prosthesis of claim 1, wherein the first valve support has an hourglass shape with a first diameter at an inflow portion thereof, a second diameter at a central portion thereof, and a third diameter at an outflow portion thereof, wherein the first and third diameters are each larger than the second diameter, and wherein the second valve support has a corresponding hourglass shape.

13. The modular valve prosthesis of claim 1, wherein the first valve support has a reverse hourglass shape with a first diameter at an inflow portion thereof, a second diameter at a central portion thereof, and a third diameter at an outflow portion thereof, wherein the first and third diameters are each smaller than the second diameter, and wherein the second valve support has a corresponding reverse hourglass shape.

14. The modular valve prosthesis of claim 1, wherein the second valve support includes a brim at an inflow end thereof, wherein the brim is parallel to a central longitudinal axis of the second valve support with the second heart valve device in a radially compressed configuration, wherein the brim is disposed radially outward at a non-zero angle with respect to the central longitudinal axis with the second heart valve device in a radially expanded configuration, and wherein in the second configuration of the second heart valve device, the brim is proximal of an inflow end of the first valve support.

15. The modular valve prosthesis of claim 14, wherein the non-zero angle is between 30 and 90 degrees.

16. The modular valve prosthesis of claim 1, wherein the second heart valve device further includes barbs extending radially outward from an outer surface of the second valve support such that with the second heart valve device in the second configuration, the barbs engage the first valve support.

17. A modular heart valve prosthesis comprising:
a first heart valve device including,
a first valve support including a first prosthetic valve disposed within the valve support, the first valve support having a first end and a second end, and the first prosthetic valve comprising leaflets having a first thickness, and
an anchoring frame surrounding the first valve support and coupled to the first valve support at the first end of the first valve support and extending longitudinally at least to the second end of the first valve support, wherein at least a portion of an inner surface of the anchoring frame is radially spaced from an outer surface of the first valve support; and
a second heart valve device including a second valve support and a second prosthetic valve disposed within the second valve support, the second prosthetic valve comprising leaflets having a second thickness, wherein the second thickness is greater than the first thickness,
wherein in a first configuration the second heart valve device is separate from the first heart valve device and in a second configuration the second heart valve device is disposed within the first valve support of the first heart valve device.

18. The modular heart valve prosthesis of claim 17, wherein the first heart valve device is self-expanding, and wherein the second heart valve device is balloon expandable.

19. The modular valve prosthesis of claim 17, wherein the first heart valve device is self-expanding, and wherein the second heart valve device is self-expanding.

20. The modular valve prosthesis of claim 17, wherein the second valve support includes a brim at an inflow end thereof, wherein the brim is parallel to a central longitudinal axis of the second valve support with the second heart valve device in a radially compressed configuration, wherein the brim is disposed radially outward at a non-zero angle with respect to the central longitudinal axis with the second heart valve device in a radially expanded configuration, and wherein in the second configuration of the second heart valve device, the brim is proximal of an inflow end of the first valve support.

21. The modular valve prosthesis of claim 20, wherein the non-zero angle is between 30 and 90 degrees.

22. The modular valve prosthesis of claim 17, wherein the second heart valve device further includes barbs extending radially outward from an outer surface of the second valve support such that with the second heart valve device in the second configuration, the barbs engage the first valve support.

23. A modular heart valve prosthesis comprising:
a first heart valve device including,
a first valve support including a first prosthetic valve disposed within the valve support, the first prosthetic valve comprising first leaflets having a first thickness in the range of about 0.04 mm to about 0.10 mm, and
an anchoring frame surrounding the first valve support and coupled to the first valve support, the anchoring frame including a first portion and a second portion; and
a second heart valve device including a second valve support and a second prosthetic valve disposed within the second valve support, the second prosthetic valve comprising second leaflets having a second thickness, wherein the second thickness is greater than the first thickness,
wherein in a first configuration the second heart valve device is separate from the first heart valve device and in a second configuration the second heart valve device is disposed within the first valve support of the first heart valve device.

24. The modular heart valve prosthesis of claim 23, wherein the first thickness is about 0.07 mm.

25. The modular heart valve prosthesis of claim 23, wherein the second thickness is in the range of about 0.35 mm to about 0.5 mm.

26. The modular heart valve prosthesis of claim 23, wherein the first heart valve device has a crimped diameter of approximately 27 Fr.

27. The modular heart valve prosthesis of claim 26, wherein the second heart valve device has a crimped diameter of approximately 14 Fr.

28. The modular valve prosthesis of claim 23, wherein the first valve support has an hourglass shape with a first diameter at an inflow portion thereof, a second diameter at a central portion thereof, and a third diameter at an outflow portion thereof, wherein the first and third diameters are each larger than the second diameter, and wherein the second valve support has a corresponding hourglass shape.

29. The modular valve prosthesis of claim 23, wherein the second valve support includes a brim at an inflow end thereof, wherein the brim is parallel to a central longitudinal axis of the second valve support with the second heart valve device in a radially compressed configuration, wherein the brim is disposed radially outward at a non-zero angle with respect to the central longitudinal axis with the second heart valve device in a radially expanded configuration, and wherein in the second configuration of the second heart valve device, the brim is proximal of an inflow end of the first valve support.

30. The modular valve prosthesis of claim 29, wherein the non-zero angle is between 30 and 90 degrees.

* * * * *